(12) United States Patent
Franklin

(10) Patent No.: US 10,960,045 B2
(45) Date of Patent: Mar. 30, 2021

(54) METHODS AND COMPOSITIONS FOR THE TREATMENT OF EPIDERMOLYSIS BULLOSA

(71) Applicant: Constant Therapeutics LLC, Cambridge, MA (US)

(72) Inventor: Richard Franklin, Cambridge, MA (US)

(73) Assignee: Constant Therapeutics LLC, Cambridge, MA (US)

( * ) Notice: Subject to any disclaimer, the term of this patent is extended or adjusted under 35 U.S.C. 154(b) by 0 days.

(21) Appl. No.: 15/768,447

(22) PCT Filed: Oct. 14, 2016

(86) PCT No.: PCT/US2016/057016
§ 371 (c)(1),
(2) Date: Apr. 13, 2018

(87) PCT Pub. No.: WO2017/066552
PCT Pub. Date: Apr. 20, 2017

(65) Prior Publication Data
US 2018/0344799 A1 Dec. 6, 2018

Related U.S. Application Data

(60) Provisional application No. 62/241,485, filed on Oct. 14, 2015.

(51) Int. Cl.
| | | |
|---|---|---|
| *A61K 38/08* | (2019.01) | |
| *A61P 17/00* | (2006.01) | |
| *C07K 7/14* | (2006.01) | |
| *C07K 7/00* | (2006.01) | |
| *A61K 31/4178* | (2006.01) | |

(52) U.S. Cl.
CPC ........ *A61K 38/085* (2013.01); *A61K 31/4178* (2013.01); *A61P 17/00* (2018.01)

(58) Field of Classification Search
CPC .. A61K 31/4178; A61K 38/085; A61K 38/08; A61P 17/00; C07K 7/14; C07K 7/00
USPC .......... 514/9.4, 21.7, 1.1; 530/316, 300, 329
See application file for complete search history.

(56) References Cited

U.S. PATENT DOCUMENTS

| | | | | |
|---|---|---|---|---|
| 5,629,292 A | * | 5/1997 | Rodgers | A61K 38/085 514/15.6 |
| 6,989,363 B1 | * | 1/2006 | Acton | C12N 9/48 514/15.6 |
| 2014/0031295 A1 | | 1/2014 | Chen et al. | |

FOREIGN PATENT DOCUMENTS

WO    WO-2013090833 A1 *  6/2013   ......... A61K 31/4178

OTHER PUBLICATIONS

Fine et al, "Inherited epidermolysis bullosa: past, present, and future," Ann. N.Y. Acad. Sci., pp. 213-222 (Year: 2010).*
Veronese et al., "PEGylation, successful approach to drug delivery," Drug Discovery Today, 10(21): 1451-1458. (Year: 2005).*
Verhoef et al, "Questioning the Use of PEGylation for Drug Delivery," Drug Deliv Transl Res., 3(6): 499-503. (Year: 2013).*
Boeira, V. L. S. Y. et al., "Inherited epidermolysis bullosa: clinical and therapeutics aspects", An Bras Dermatol., vol. 88, No. 2, Mar. 2013, pp. 185-198.
Database Medline [Online] U.S. National Library of Medicine (NLM), Bethesda, MD US, Aug. 2016, HAS Cristina: "Molecular therapies for inherited epidermolysis bullosa", Database Accession No. NLM27149615, 1 page.

\* cited by examiner

*Primary Examiner* — Julie Ha
(74) *Attorney, Agent, or Firm* — Proskauer Rose LLP; Fangli Chen; Julio J. Mendez

(57) ABSTRACT

A method of treating epidermolysis bullosa comprising administering to a subject suffering from epidermolysis bullosa an angiotensin (1-7) peptide is described. In some embodiments, methods of treating a complication of epidermolysis bullosa are described including administering to a subject suffering from one or more complications of epidermolysis bullosa an angiotensin (1-7) peptide, wherein the administration results in a reduction in the intensity, severity, duration, or frequency of at least one symptom or feature of the one or more complications of epidermolysis bullosa.

22 Claims, 8 Drawing Sheets

Specification includes a Sequence Listing.

A

B

SEQUENCE LISTING

```
<160> NUMBER OF SEQ ID NOS: 23

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 1

Asp Arg Val Tyr Ile His Pro
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 2

Asp Arg Val Ser Ile His Cys
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Chemically
``` synthesized peptide

<400> SEQUENCE: 3

Ala Arg Val Ser Ile His Cys
1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 4

Asp Arg Val Tyr Ile His Pro Phe His Leu Val Ile
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (1)..(1)
<223> OTHER INFORMATION: Any amino acid or a dicarboxylic acid
<220> FEATURE:
<221> NAME/KEY: MOD_RES
<222> LOCATION: (2)..(2)
<223> OTHER INFORMATION: Arg, Lys, Ala, Cit, Orn, acSer, Sar, D-Arg, or
      D-Lys
<220> FEATURE:
<221> NAME/KEY: MOD_RES
<222> LOCATION: (3)..(3)
<223> OTHER INFORMATION: Val, Ala, Leu, Nle, Ile, Gly, Lys, Pro,
      HydroxyPro, Aib, Acpc, or Tyr
<220> FEATURE:
<221> NAME/KEY: MOD_RES
<222> LOCATION: (4)..(4)
<223> OTHER INFORMATION: Tyr, Tyr(PO3), Thr, Ser, homoSer, azaTyr, or
      Ala
<220> FEATURE:
<221> NAME/KEY: MOD_RES
<222> LOCATION: (5)..(5)
<223> OTHER INFORMATION: Ile, Ala, Leu, norLeu, Val, or Gly
<220> FEATURE:
<221> NAME/KEY: MOD_RES
<222> LOCATION: (6)..(6)
<223> OTHER INFORMATION: His, Arg, or 6-NH2-Phe
<220> FEATURE:
<221> NAME/KEY: MOD_RES
<222> LOCATION: (7)..(7)
<223> OTHER INFORMATION: Cys, Pro, or Ala
<220> FEATURE:
<223> OTHER INFORMATION: See specification as filed for detailed
      description of substitutions and preferred embodiments

<400> SEQUENCE: 5

Xaa Xaa Xaa Xaa Xaa Xaa Xaa
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES

```
<222> LOCATION: (3)..(3)
<223> OTHER INFORMATION: Nle

<400> SEQUENCE: 6

Asp Arg Leu Tyr Ile His Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (4)..(4)
<223> OTHER INFORMATION: Any amino acid forming a thioether bridge
<220> FEATURE:
<221> NAME/KEY: MISC_FEATURE
<222> LOCATION: (4)..(7)
<223> OTHER INFORMATION: Thioether bridge
<220> FEATURE:
<221> NAME/KEY: MOD_RES
<222> LOCATION: (7)..(7)
<223> OTHER INFORMATION: Any amino acid forming a thioether bridge
<220> FEATURE:
<223> OTHER INFORMATION: See specification as filed for detailed
      description of substitutions and preferred embodiments

<400> SEQUENCE: 7

Asp Arg Val Xaa Ile His Xaa
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid forming a thioether bridge
<220> FEATURE:
<221> NAME/KEY: MISC_FEATURE
<222> LOCATION: (4)..(7)
<223> OTHER INFORMATION: Thioether bridge
<220> FEATURE:
<221> NAME/KEY: MOD_RES
<222> LOCATION: (7)..(7)
<223> OTHER INFORMATION: Any amino acid forming a thioether bridge
<220> FEATURE:
<223> OTHER INFORMATION: See specification as filed for detailed
      description of substitutions and preferred embodiments

<400> SEQUENCE: 8

Asp Arg Leu Xaa Ile His Xaa Phe His Leu
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
```

```
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid forming a thioether bridge
<220> FEATURE:
<221> NAME/KEY: MISC_FEATURE
<222> LOCATION: (4)..(7)
<223> OTHER INFORMATION: Thioether bridge
<220> FEATURE:
<221> NAME/KEY: MOD_RES
<222> LOCATION: (7)..(7)
<223> OTHER INFORMATION: Any amino acid forming a thioether bridge
<220> FEATURE:
<223> OTHER INFORMATION: See specification as filed for detailed
      description of substitutions and preferred embodiments

<400> SEQUENCE: 9

Asp Arg Leu Xaa Ile His Xaa Phe
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: Any amino acid forming a thioether bridge
<220> FEATURE:
<221> NAME/KEY: MISC_FEATURE
<222> LOCATION: (3)..(6)
<223> OTHER INFORMATION: Thioether bridge
<220> FEATURE:
<221> NAME/KEY: MOD_RES
<222> LOCATION: (6)..(6)
<223> OTHER INFORMATION: Any amino acid forming a thioether bridge
<220> FEATURE:
<223> OTHER INFORMATION: See specification as filed for detailed
      description of substitutions and preferred embodiments

<400> SEQUENCE: 10

Arg Leu Xaa Ile His Xaa Phe
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: Any amino acid forming a thioether bridge
<220> FEATURE:
<221> NAME/KEY: MISC_FEATURE
<222> LOCATION: (2)..(5)
<223> OTHER INFORMATION: Thioether bridge
<220> FEATURE:
<221> NAME/KEY: MOD_RES
```

```
<222> LOCATION: (5)..(5)
<223> OTHER INFORMATION: Any amino acid forming a thioether bridge
<220> FEATURE:
<223> OTHER INFORMATION: See specification as filed for detailed
      description of substitutions and preferred embodiments

<400> SEQUENCE: 11

Leu Xaa Ile His Xaa Phe
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid forming a thioether bridge
<220> FEATURE:
<221> NAME/KEY: MISC_FEATURE
<222> LOCATION: (4)..(7)
<223> OTHER INFORMATION: Thioether bridge
<220> FEATURE:
<221> NAME/KEY: MOD_RES
<222> LOCATION: (7)..(7)
<223> OTHER INFORMATION: Any amino acid forming a thioether bridge
<220> FEATURE:
<223> OTHER INFORMATION: See specification as filed for detailed
      description of substitutions and preferred embodiments

<400> SEQUENCE: 12

Asp Arg Leu Xaa Ile His Xaa
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid forming a thioether bridge
<220> FEATURE:
<221> NAME/KEY: MISC_FEATURE
<222> LOCATION: (4)..(7)
<223> OTHER INFORMATION: Thioether bridge
<220> FEATURE:
<221> NAME/KEY: MOD_RES
<222> LOCATION: (7)..(7)
<223> OTHER INFORMATION: Any amino acid forming a thioether bridge
<220> FEATURE:
<223> OTHER INFORMATION: See specification as filed for detailed
      description of substitutions and preferred embodiments

<400> SEQUENCE: 13

Asp Arg Leu Xaa Ile His Xaa Phe His
1               5

<210> SEQ ID NO 14
```

```
<211> LENGTH: 7
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any positively charged amino acid
<220> FEATURE:
<221> NAME/KEY: MOD_RES
<222> LOCATION: (3)..(3)
<223> OTHER INFORMATION: Any aliphatic amino acid
<220> FEATURE:
<221> NAME/KEY: MOD_RES
<222> LOCATION: (4)..(4)
<223> OTHER INFORMATION: Any amino acid forming a thioether bridge
<220> FEATURE:
<221> NAME/KEY: MISC_FEATURE
<222> LOCATION: (4)..(7)
<223> OTHER INFORMATION: Thioether bridge
<220> FEATURE:
<221> NAME/KEY: MOD_RES
<222> LOCATION: (5)..(5)
<223> OTHER INFORMATION: Any aliphatic amino acid
<220> FEATURE:
<221> NAME/KEY: MOD_RES
<222> LOCATION: (7)..(7)
<223> OTHER INFORMATION: Any amino acid forming a thioether bridge
<220> FEATURE:
<223> OTHER INFORMATION: See specification as filed for detailed
      description of substitutions and preferred embodiments

<400> SEQUENCE: 14

Xaa Xaa Xaa Xaa Xaa His Xaa
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (4)..(4)
<223> OTHER INFORMATION: Abu

<400> SEQUENCE: 15

Asp Arg Val Xaa Ile His Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 16

Asp Arg Val Ala Ile His Ala
1               5

<210> SEQ ID NO 17
<211> LENGTH: 10
<212> TYPE: PRT
```

```
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (1)..(1)
<223> OTHER INFORMATION: Any amino acid or absent
<220> FEATURE:
<221> NAME/KEY: MOD_RES
<222> LOCATION: (2)..(2)
<223> OTHER INFORMATION: Any positively charged amino acid or absent
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid forming a thioether bridge
<220> FEATURE:
<221> NAME/KEY: MISC_FEATURE
<222> LOCATION: (4)..(7)
<223> OTHER INFORMATION: Thioether bridge
<220> FEATURE:
<221> NAME/KEY: MOD_RES
<222> LOCATION: (5)..(5)
<223> OTHER INFORMATION: Any aliphatic amino acid
<220> FEATURE:
<221> NAME/KEY: MOD_RES
<222> LOCATION: (7)..(7)
<223> OTHER INFORMATION: Any amino acid forming a thioether bridge
<220> FEATURE:
<221> NAME/KEY: MOD_RES
<222> LOCATION: (8)..(8)
<223> OTHER INFORMATION: Ala, Arg, Asn, Asp, Cys, Gln, Glu, Gly, His,
      Ile, Leu, Lys, Met, Phe, Ser, Thr, Trp, Tyr, Val, or absent
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MOD_RES
<222> LOCATION: (10)..(10)
<223> OTHER INFORMATION: Any aliphatic residue or absent
<220> FEATURE:
<223> OTHER INFORMATION: See specification as filed for detailed
      description of substitutions and preferred embodiments

<400> SEQUENCE: 17

Xaa Xaa Leu Xaa Xaa His Xaa Xaa His Xaa
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Abu

<400> SEQUENCE: 18

Asp Arg Leu Xaa Ile His Ala
1               5

<210> SEQ ID NO 19
<211> LENGTH: 7
```

```
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (3)..(3)
<223> OTHER INFORMATION: Nle

<400> SEQUENCE: 19

Asp Arg Leu Ala Ile His Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Abu

<400> SEQUENCE: 20

Asp Arg Leu Xaa Ile His Ala Ile
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (3)..(3)
<223> OTHER INFORMATION: Nle

<400> SEQUENCE: 21

Asp Arg Leu Ala Ile His Ala Ile
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 22

Asp Arg Val Tyr Ile His Pro Phe His
1               5

<210> SEQ ID NO 23
<211> LENGTH: 7
<212> TYPE: PRT
<213> ORGANISM: Artificial Sequence
<220> FEATURE:
```

```
<223> OTHER INFORMATION: Description of Artificial Sequence: Chemically
      synthesized peptide

<400> SEQUENCE: 23

Ala Arg Val Tyr Ile His Pro
1               5
```

METHODS AND COMPOSITIONS FOR THE TREATMENT OF EPIDERMOLYSIS BULLOSA

CROSS REFERENCE TO RELATED APPLICATIONS

This application is a 35 U.S.C. § 371 National Stage Application of International Application No. PCT/US16/57016, filed Oct. 14, 2016, which claims priority to U.S. Provisional Patent Application Ser. No. 62/241,485, filed on Oct. 14, 2015, the disclosures of each of which are hereby incorporated by reference in their entirety.

INCORPORATION-BY-REFERENCE OF SEQUENCE LISTING

The content of the ASCII text file named "TXP-023US-_SL.txt", which was created on Oct. 23, 2020 and is 11,300 bytes in size, is hereby incorporated by reference in its entirety.

BACKGROUND

Epidermolysis bullosa (EB), refers to a group of inherited connective tissue disorders characterized in part by the formation of blisters after very minor trauma, even for no apparent cause. While the exact prevalence is unknown, it is estimated that EB is present at an incidence rate of approximately 1/50,000. The genetic basis of EB appears to be highly complex, with over 300 genetic mutations being implicated in the disease.

SUMMARY OF THE INVENTION

The present invention provides, among other things, methods and compositions for treating an epidermolysis bullosa, including, but not limited to, epidermolysis bullosa simplex (EBS), junctional epidermolysis bullosa (JEB), dystrophic epidermolysis bullosa (DEB), epidermolysis bullosa acquisita (EBA), and combinations thereof. Methods of treating an epidermolysis bullosa include administering to a subject suffering from an epidermolysis bullosa an angiotensin (1-7) peptide.

The present invention also provides, in some embodiments, methods of treating a complication of epidermolysis bullosa including administering to a subject suffering from one or more complications of epidermolysis bullosa an angiotensin (1-7) peptide, wherein the administration results in a reduction in the intensity, severity, duration, or frequency of at least one sign, symptom or feature of the one or more complications of epidermolysis bullosa. In some embodiments, the one or more complications of epidermolysis bullosa is selected from a infection, sepsis, deformities, malnutrition and anemia, dehydration, constipation, eye disorders, and skin cancer.

Various embodiments may be administered via any medically appropriate route. In some embodiments, the administration is via parenteral, oral, or rectal administration. In some embodiments, parenteral administration is intravenous, subcutaneous, inhalation, intradermal, transdermal, and/or transmucosal administration.

The treatment of various types of epidermolysis bullosa and epidermolysis bullosa-related conditions are contemplated according to various embodiments. In some embodiments, an epidermolysis bullosa is one or more of epidermolysis bullosa simplex (EBS), junctional epidermolysis bullosa (JEB), dystrophic epidermolysis bullosa (DEB), epidermolysis bullosa acquisita (EBA), and combinations thereof.

In some embodiments, the angiotensin (1-7) peptide is administered at an effective dose periodically at an administration interval such that at least one symptom or feature of epidermolysis bullosa is reduced in intensity, severity, duration, or frequency or has delayed onset. In some embodiments, the angiotensin (1-7) peptide is administered once per day. In some embodiments, the angiotensin (1-7) peptide is administered once per week. In some embodiments, the angiotensin (1-7) peptide is administered three times per month. In some embodiments, the angiotensin (1-7) peptide is administered twice per month. In some embodiments, the angiotensin (1-7) peptide is administered once per month.

Any of a variety of doses may be used according to various embodiments. In some embodiments, the angiotensin (1-7) peptide is administered at an effective dose ranging from about 1-1,000 µg/kg/day. In some embodiments, the angiotensin (1-7) peptide is administered at an effective dose ranging from about 50-500 µg/kg/day. In some embodiments, the angiotensin (1-7) peptide is administered at an effective dose ranging from about 1-60 µg/kg/day.

In some embodiments, the angiotensin (1-7) peptide comprises the naturally-occurring Angiotensin (1-7) amino acid sequence of $Asp^1$-$Arg^2$-$Val^3$-$Tyr^4$-$Ile^5$-$His^6$-$Pro^7$ (SEQ ID NO: 1).

In some embodiments, the angiotensin (1-7) peptide is a functional equivalent of SEQ ID NO: 1. In some embodiments, the functional equivalent is a linear peptide. In some embodiments, the linear peptide comprises a sequence that includes at least four amino acids from the seven amino acids that appear in the naturally-occurring Angiotensin (1-7), wherein the at least four amino acids maintain their relative positions as they appear in the naturally-occurring Angiotensin (1-7). In some embodiments, the linear peptide contains 4-25 amino acids. In some embodiments, the linear peptide is a fragment of the naturally-occurring Angiotensin (1-7). In some embodiments, the linear peptide contains amino acid substitutions, deletions and/or insertions in the naturally-occurring Angiotensin (1-7). In some embodiments, the linear peptide has an amino acid sequence of $Asp^1$-$Arg^2$-$Val^3$-$Ser^4$-$Ile^5$-$His^6$-$Cys^7$ (SEQ ID NO: 2). In some embodiments, the linear peptide has an amino acid sequence of $Ala^1$-$Arg^2$-$Val^3$-$Ser^4$-$Ile^5$-$His^6$-$Cys^7$ (SEQ ID NO: 3). In some embodiments, an angiotensin (1-7) peptide is a non-cyclic peptide.

In some embodiments, the angiotensin (1-7) peptide comprises one or more chemical modifications to increase protease resistance, serum stability and/or bioavailability. In some embodiments, the one or more chemical modifications comprise pegylation.

In some embodiments, the angiotensin (1-7) peptide is a non-peptidic angiotensin(1-7) receptor agonist. In some embodiments, the non-peptidic angiotensin(1-7) receptor agonist is a compound with the following structure:

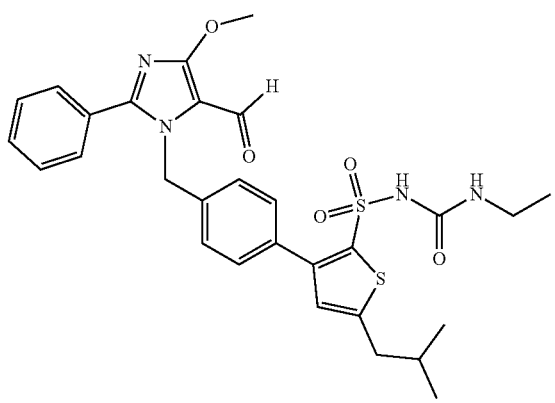 [SMILES: CCNC(=O)NS(=O)(=O)c1sc(CC(C)C)cc1-c1ccc(Cn2c(-c3ccccc3)nc(OC)c2C=O)cc1]

or a pharmaceutically acceptable salt thereof.

As used in this application, the terms "about" and "approximately" are used as equivalents. Any citations to publications, patents, or patent applications herein are incorporated by reference in their entirety. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

FIG. 1A consists of images of the right forepaw of a RDEB mouse before and after treatment with angiotensin (1-7). RDEB mice display a fibrosis-driven loss and fusion of digits over time, and angiotensin (1-7) treatment reduced the expression of this deleterious phenotype. FIG. 1B is a graph of the average toe length of RDEB mice treated with angiotensin (1-7) peptide for four weeks ("Tarix") or a vehicle control ("Vehicle") as a percentage of average toe length before treatment. Angiotensin (1-7) treatment resulted in a significant reduction in the decrease in toe length of RDEB mice relative to vehicle-treated controls.

DEFINITIONS

Figure 1:
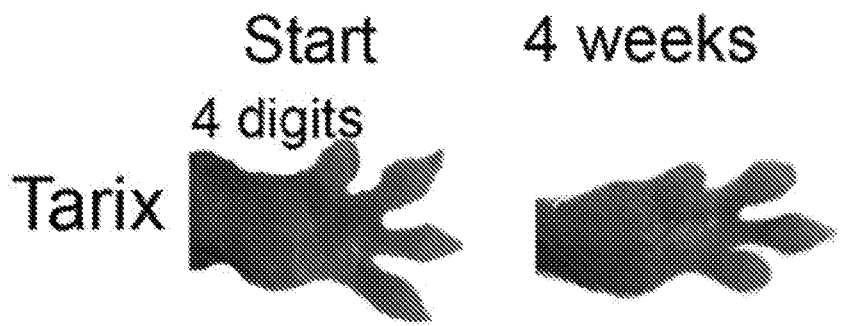
FIGS. 1A-1B. Recessive dystrophic epidermolysis bullosa (RDEB) mice were treated with angiotensin (1-7) peptide for four weeks.
Figure 1:
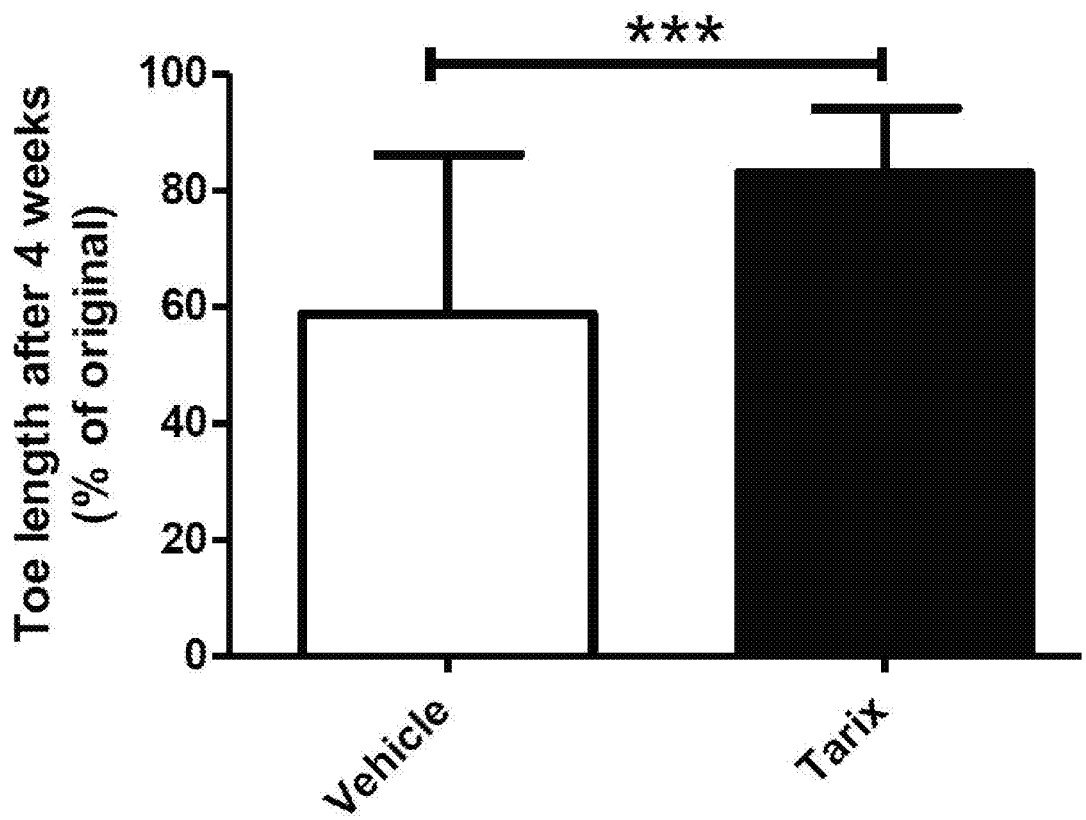

In order for the present invention to be more readily understood, certain terms are first defined below. Additional definitions for the following terms and other terms are set forth throughout the specification.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion. In certain embodiments, a peptide has no intrinsic biological activity but that inhibits the effects of one or more naturally-occurring angiotensin compounds is considered to be biologically active.

Carrier or diluent: As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Complication: As used herein, the term "complication" refers to an unfavorable evolution of a disease including the development of one or more signs, symptoms or, in some embodiments, even new pathological changes that manifest for a sustained period of time (e.g., weeks, months or years). In some embodiments, complication(s) may include a progression of a sign, symptom or other pathological change, for example, a minor memory loss growing worse over time, or a difficulty with one or more motor functions progressing to paralysis.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent (e.g., an angiotensin (1-7) peptide) has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, the therapeutic agent is administered continuously over a predetermined period. In some embodiments, the therapeutic agent is administered once a day (QD) or twice a day (BID).

Functional equivalent or derivative: As used herein, the term "functional equivalent" or "functional derivative" denotes, in the context of a functional derivative of an amino acid sequence, a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Prevent: As used herein, the term "prevent" or "prevention", when used in connection with the occurrence of a disease, disorder, and/or condition, refers to reducing the risk of developing the disease, disorder and/or condition. See the definition of "risk."

Polypeptide: The term "polypeptide" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., epidermolysis bullosa). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., epidermolysis bullosa). In some embodiments a reference sample or group of reference samples are from individuals comparable to a particular individual. In some embodiments, relative risk is 0, 1, 2, 3, 4, 5, 6, 7, 8, 9, 10, or more.

Sign: As used herein, the term "sign" refers to a departure from normal body function that indicates the presence of a disease or abnormality that is noticed by a person other than the patient (as opposed to a symptom, see below).

Stability: As used herein, the term "stable" refers to the ability of the therapeutic agent to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In certain embodiments, pharmaceutical compositions described herein have been formulated such that they are capable of stabilizing, or alternatively slowing or preventing the degradation, of one or more therapeutic agents formulated therewith. In the context of a formulation a stable formulation is one in which the therapeutic agent therein essentially retains its physical and/or chemical integrity and biological activity upon storage and during processes (such as freeze/thaw, mechanical mixing and lyophilization).

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, epidermolysis bullosa) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Symptom: As used herein, the term "symptom" refers to a departure from normal body function that indicates the presence of a disease or abnormality that is noticed by the subject or patient.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION OF CERTAIN EMBODIMENTS

The present invention provides, among other things, methods and compositions for treating epidermolysis bullosa and related conditions. In some embodiments, an epidermolysis bullosa may be epidermolysis bullosa simplex (EBS), junctional epidermolysis bullosa (JEB), dystrophic epidermolysis bullosa (DEB), epidermolysis bullosa acquisita (EBA), and combinations thereof. Provided methods of treating epidermolysis bullosa include administering to a subject suffering from an epidermolysis bullosa an angiotensin (1-7) peptide.

Various aspects of the invention are described in detail in the following sections. The use of sections is not meant to limit the invention. Each section can apply to any aspect of the invention. In this application, the use of "or" means "and/or" unless stated otherwise.

Epidermolysis Bullosa

Epidermolysis bullosa is a group of rare diseases that cause the skin to blister in response to even the mildest trauma. Signs and symptoms of epidermolysis bullosa include: fluid-filled blisters on the skin, especially on the hands and feet due to friction, deformity or loss of fingernails and toenails, internal blistering, including on the vocal cords, esophagus and upper airway, skin thickening on the palms and the soles of the feet, scalp blistering, scarring and hair loss (scarring alopecia), thin-appearing skin (atrophic scarring), tiny white skin bumps or pimples (milia), dental problems, such as tooth decay from poorly formed enamel, and difficulty swallowing (dysphagia).

Epidermolysis bullosa is usually inherited. Researchers have identified more than a dozen genes involved with skin formation that, if defective, may cause a type of epidermolysis bullosa. The skin is made up of an outer layer (epidermis) and an underlying layer (dermis). The area where the layers meet is called the basement membrane zone. The different types of epidermolysis bullosa are defined by where in these layers the blisters form.

Complications associated with epidermolysis bullosa include infection, sepsis, deformities, malnutrition and anemia, dehydration, constipation, eye disorders, skin cancer and death.

While the condition usually shows up in infancy or early childhood, some people don't develop signs and symptoms until adolescence or early adulthood. Epidermolysis bullosa has no cure, though mild forms may improve with age. Treatment focuses on addressing the symptoms, such as infection and itching, and preventing pain and wounds. Severe forms may cause serious complications and can be fatal.

Treatment of epidermolysis bullosa aims to prevent complications and ease the pain of the blisters with appropriate wound care. The condition often progresses despite treatment, sometimes causing serious complications and death. Addressing the many aspects of wound care usually requires a multidisciplinary approach. Medication options include those that can help control pain and itching, medications that address complications such as sepsis (e.g., antibiotics), and medications that reduce inflammation (e.g., a corticosteroid). Surgical options include surgery to correct abnormal motion (e.g., surgery to correct fusing of finger or toes or abnormal bends in the joints), surgery to improve the ability to eat a healthy diet (e.g., surgical dilation of the esophagus or placement of a feeding tube), and skin grafts (e.g., OrCel composite cultured skin). Working with a rehabilitation specialist (physical therapist, occupational therapist) can help ease the limitations on motion caused by scarring and shortening of the skin (contracture). A rehabilitation specialist can also give guidance on the best ways to stay safe while going about daily activities. Swimming may also be helpful in preserving or regaining mobility. Other potential treatments to treat and relieve symptoms include gene therapy, bone marrow transplantation, protein replacement therapy, cell-based therapies, and/or combinations thereof, among others.

Epidermolysis Bullosa Simplex (EBS)

Epidermolysis bullosa simplex (EBS) is the most common form of epidermolysis bullosa. There are many types of EBS and most are caused by an autosomal dominant gene mutation that leads to a defective keratin protein. Keratin proteins function as the scaffolding for the skin, and so when this scaffolding is not formed correctly, the skin is more likely to fall apart and form blisters. EBS can be split up into two main types, Generalized and Localized. In Generalized EBS, blistering occurs all over the body, while in the more common Localized EBS, blistering only occurs in areas that receive the most trauma, usually the hands and feet. In EBS, the gene that helps produce a fibrous protein (keratin) in the top layer of skin is faulty. The condition causes blistering in the epidermis. In this mild type of epidermolysis bullosa, the blisters usually don't result in scars.

Junctional Epidermolysis Bullosa (JEB)

Junctional epidermolysis bullosa (JEB) is an autosomal recessive condition that is caused by mutations in genes that code for proteins (collagen17 or laminin-5) that help form thread-like fibers (fibrils) that attach the epidermis to the basement membrane. Without them the skin separates easily, causing blisters. There are many types of JEB and all of them cause widespread blistering. Some forms of JEB improve as the patient gets older, while a rare form of JEB can be fatal in infancy. This type is usually severe and becomes apparent at birth. A baby with this condition may develop a hoarse-sounding cry from continual blistering and scarring of the vocal cords.

Dystrophic Epidermolysis Bullosa (DEB)

Dystrophic epidermolysis bullosa (DEB) is caused by a mutation in the collagen7 gene and can be dominant or recessive. The collagen gene codes for the collagen7 protein that anchors the deeper layer of skin, called the dermis, to the epidermis, or superficial layer of skin. When an individual has an abnormal collagen protein, the skin is fragile and separates easily, forming blisters. Both dominant and recessive forms of DEB cause scarring. An individual with dominant DEB generally experiences mild to moderate blistering of the skin, but only a small amount of blistering of the mouth, esophagus, and GI tract. This type rarely causes deformity of the hands or feet.

The recessive form of DEB is the most severe, chronic type of epidermolysis bullosa. Blistering begins at birth or shortly afterwards. Much of the skin is covered in blisters and there is extensive internal blistering. Children can develop deformities caused by the recurrent scarring of the fingers and toes (pseudosyndactyly) and the hands and arms become fixed in stiff positions (contractures). It is painfully difficult for a child with recessive Dystrophic EB to ingest food due to the internal blistering that occurs in the mouth, esophagus, and gastrointestinal tract.

Epidermolysis Bullosa Acquisita (EBA)

Epidermolysis bullosa acquisita (EBA) is a rare type of epidermolysis bullosa that isn't inherited. It is a chronic autoimmune subepidermal blistering disease of the skin and mucus membranes that can occur in people of all ages. Initial manifestations are highly variable, sometimes resembling those of bullous pemphigoid. Bullous lesions are most often in areas subject to minor trauma, such as the extensor aspects of the elbows and the dorsal aspects of the hands and feet. Healing usually causes scars, milia (superficial epidermal inclusion cysts), and hyperpigmentation. However, a subset of EBA patients has a generalized inflammatory skin blister phenotype. Immunologically, EBA is characterized by the presence of immunoglobulin G (IgG) autoantibodies (in most patients) targeting the noncollagenous (NC1) domain of type VII collagen, the major component of anchoring fibrils that connect the basement membrane to dermal structures. The loss of anchoring fibrils leads to the formation of blisters just under the epidermis within an area known as the lamina densa.

Some patients with EBA have been reported to have other health problems, most often Crohn disease, systemic lupus erythematosus, amyloidosis, multiple myeloma and rarely carcinoma of the lung and lymphoma. Other patients only have a skin problem. The reason why autoantibodies are produced is unknown.

Angiotensin (1-7) Peptides

As used herein, the term "angiotensin (1-7) peptide" refers to both naturally-occurring Angiotensin (1-7) and any functional equivalent, analogue or derivative of naturally-occurring Angiotensin (1-7). As used herein, "peptide" and "polypeptide" are interchangeable terms and refer to two or more amino acids bound together by a peptide bond. As used herein, the terms "peptide" and "polypeptide" include both linear and cyclic peptide. The terms "angiotensin-(1-7)", "Angiotensin-(1-7)", and "Ang-(1-7)" are used interchangeably.

Naturally-Occurring Angiotensin (1-7)

Naturally-occurring Angiotensin (1-7) (also referred to as Ang-(1-7)) is a seven amino acid peptide shown below:

$$\text{Asp}^1\text{-Arg}^2\text{-Val}^3\text{-Tyr}^4\text{-Ile}^5\text{-His}^6\text{-Pro}^7 \quad \text{(SEQ ID NO: 1)}$$

It is part of the renin-angiotensin system and is converted from a precursor, also known as Angiotensinogen, which is an α-2-globulin that is produced constitutively and released into the circulation mainly by the liver. Angiotensinogen is a member of the serpin family and also known as renin substrate. Human angiotensinogen is 452 amino acids long, but other species have angiotensinogen of varying sizes. Typically, the first 12 amino acids are the most important for angiotensin activity:

$$\text{Asp}^1\text{-Arg}^2\text{-Val}^3\text{-Tyr}^4\text{-Ile}^5\text{-His}^6\text{-Pro}^7\text{-Phe}^8\text{-His}^9\text{-Leu}^{10}\text{-Val}^{11}\text{-Ile}^{12} \quad \text{(SEQ ID NO: 4)}$$

Different types of angiotensin may be formed by the action of various enzymes. For example, Angiotensin (1-7) is generated by action of Angiotensin-converting enzyme 2 (ACE 2).

Ang-(1-7) is an endogenous ligand for Mas receptors. Mas receptors are G-protein coupled receptor containing seven transmembrane spanning regions. As used herein, the term "angiotensin-(1-7) receptor" encompasses the G Protein-Coupled Mas Receptors.

As used herein, the term "naturally-occurring Angiotensin (1-7)" includes any Angiotensin (1-7) peptide purified from natural sources and any recombinantly produced or chemically synthesized peptides that have an amino acid sequence identical to that of the naturally-occurring Angiotensin (1-7).

Functional Equivalents, Analogs or Derivatives of Ang-(1-7)

In some embodiments, an angiotensin (1-7) peptide suitable for the present invention is a functional equivalent of naturally-occurring Ang-(1-7). As used herein, a functional equivalent of naturally-occurring Ang-(1-7) refers to any peptide that shares amino acid sequence identity to the naturally-occurring Ang-(1-7) and retain substantially the same or similar activity as the naturally-occurring Ang-(1-7). For example, in some embodiments, a functional equivalent of naturally-occurring Ang-(1-7) described herein has pro-angiogenic activity as determined using methods described herein or known in the art, or an activity such as nitric oxide release, vasodilation, improved endothelial function, antidiuresis, or one of the other properties discussed herein, that positively impacts angiogenesis. In some embodiments, a functional equivalent of naturally-occurring Ang-(1-7) described herein can bind to or activate an angiotensin-(1-7) receptor (e.g., the G protein-coupled Mas receptor) as determined using various assays described herein or known in the art. In some embodiments, a functional equivalent of Ang-(1-7) is also referred to as an angiotensin (1-7) analogue or derivative, or functional derivative. In some embodiments, a functional equivalent of Ang-(1-7) is a non-cyclic peptide.

Typically, a functional equivalent of angiotensin (1-7) shares amino acid sequence similarity to the naturally-occurring Ang-(1-7). In some embodiments, a functional equivalent of Ang-(1-7) according to the invention contains a sequence that includes at least 3 (e.g., at least 4, at least 5, at least 6, at least 7) amino acids from the seven amino acids that appear in the naturally-occurring Ang-(1-7), wherein the at least 3 (e.g., at least 4, at least 5, at least 6, or at least 7) amino acids maintain their relative positions and/or spacing as they appear in the naturally-occurring Ang-(1-7).

In some embodiments, a functional equivalent of Ang-(1-7) may encompass any peptide that contains a sequence at least 50% (e.g., at least 60%, 70%, 80%, or 90%) identical to the amino acid sequence of naturally-occurring Ang-(1-7). Percentage of amino acid sequence identity can be determined by alignment of amino acid sequences. Alignment of amino acid sequences can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., Methods in Enzymology 266, 460-480 (1996); http://blast.wustl/edu/blast/README.html). WU-BLAST-2 uses several search parameters, most of which are set to the default values. The adjustable parameters are set with the following values: overlap span=1, overlap fraction=0.125, word threshold (T)=11. HSP score (S) and HSP S2 parameters are dynamic values and are established by the program itself, depending upon the composition of the particular sequence, however, the minimum values may be adjusted and are set as indicated above.

In some embodiments, a functional equivalent, analogue or derivative of Ang-(1-7) is a fragment of the naturally-occurring Ang-(1-7). In some embodiments, a functional equivalent, analogue or derivative of Ang-(1-7) contains amino acid substitutions, deletions and/or insertions in the naturally-occurring Ang-(1-7). Ang-(1-7) functional equivalents, analogues or derivatives can be made by altering the amino acid sequences by substitutions, additions, and/or deletions. For example, one or more amino acid residues within the sequence of the naturally-occurring Ang-(1-7) (SEQ ID NO: 1) can be substituted by another amino acid of a similar polarity, which acts as a functional equivalent, resulting in a silent alteration. Substitution for an amino acid within the sequence may be selected from other members of the class to which the amino acid belongs. For example, the positively charged (basic) amino acids include arginine, lysine, and histidine. The nonpolar (hydrophobic) amino acids include leucine, isoleucine, alanine, phenylalanine, valine, proline, tryptophan, and methionine. The uncharged polar amino acids include serine, threonine, cysteine, tyrosine, asparagine, and glutamine. The negatively charged (acid) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions. For example, the amino acid sequence of a peptide inhibitor can be modified or substituted.

Examples of Ang-(1-7) functional equivalents, analogues and derivatives are described in the section entitled "Exemplary Angiotensin(1-7) Peptides" below.

An angiotensin-(1-7) peptide can be of any length. In some embodiments, an angiotensin-(1-7) peptide according to the present invention can contain, for example, from 4-25 amino acids (e.g., 4-20, 4-15, 4-14, 4-13, 4-12, 4-11, 4-10, 4-9, 4-8, 4-7 amino acids). In some embodiments, the linear peptide contains 4, 5, 6, 7, 8, 9, 10, 11, 12, 13, 14, 16, 17, 18, 19, 20, 21, 22, 23, 24, or 25 amino acids.

In some embodiments, an angiotensin-(1-7) peptide contains one or more modifications to increase protease resistance, serum stability and/or bioavailability. In some embodiments, suitable modifications are selected from pegylation, acetylation, glycosylation, biotinylation, substitution with D-amino acid and/or un-natural amino acid, and/or cyclization of the peptide.

As used herein, the term "amino acid," in its broadest sense, refers to any compound and/or substance that can be incorporated into a polypeptide chain. In certain embodiments, an amino acid has the general structure $H_2N$—$C(H)$(R)—COOH. In certain embodiments, an amino acid is a naturally-occurring amino acid. In certain embodiments, an amino acid is a synthetic or un-natural amino acid (e.g., α,α-disubstituted amino acids, N-alkyl amino acids); in some embodiments, an amino acid is a d-amino acid; in certain embodiments, an amino acid is an l-amino acid.

"Standard amino acid" refers to any of the twenty standard amino acids commonly found in naturally occurring peptides including both l- and d-amino acids which are both incorporated in peptides in nature. "Nonstandard" or "unconventional amino acid" refers to any amino acid, other than the standard amino acids, regardless of whether it is prepared synthetically or obtained from a natural source. As used herein, "synthetic or un-natural amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical groups that can change the peptide's circulating half-life without adversely affecting its activity. Examples of unconventional or un-natural amino acids include, but are not limited to, citrulline, ornithine, norleucine, norvaline, 4-(E)-butenyl-4(R)-methyl-N-methylthreonine (MeBmt), N-methyl-leucine (MeLeu), aminoisobutyric acid, statine, and N-methyl-alanine (MeAla). Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

In certain embodiments, angiotensin-(1-7) peptides contain one or more L-amino acids, D-amino acids, and/or un-natural amino acids.

In addition to peptides containing only naturally occurring amino acids, peptidomimetics or peptide analogs are also encompassed by the present invention. Peptide analogs are commonly used in the pharmaceutical industry as non-peptide drugs with properties analogous to those of the template peptide. The non-peptide compounds are termed "peptide mimetics" or peptidomimetics (Fauchere et al., Infect. Immun. 54:283-287 (1986); Evans et al., J. Med. Chem. 30:1229-1239 (1987)). Peptide mimetics that are structurally related to therapeutically useful peptides and may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —$CH_2NH$—, —$CH_2S$—, —$CH_2$—$CH_2$—, —CH=CH— (cis and trans), —$CH_2SO$—, —CH(OH)$CH_2$—, —COCH$_2$— etc., by methods well known in the art (Spatola, Peptide Backbone Modifications, Vega Data, 1(3):267 (1983); Spatola et al. Life Sci. 38:1243-1249 (1986); Hudson et al. Int. J. Pept. Res. 14:177-185 (1979); and Weinstein. B., 1983, Chemistry and Biochemistry, of Amino Acids, Peptides and Proteins, Weinstein eds, Marcel Dekker, New-York). Such peptide mimetics may have significant advantages over naturally-occurring polypeptides including more economical production, greater chemical stability, enhanced pharmacological properties (e.g., half-life, absorption, potency, efficiency, etc.), reduced antigenicity and others.

Ang-(1-7) peptides also include other types of peptide derivatives containing additional chemical moieties not normally part of the peptide, provided that the derivative retains the desired functional activity of the peptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives; and (6) derivatives conjugated to a polyethylene glycol (PEG) chain.

Ang-(1-7) peptides may be obtained by any method of peptide synthesis known to those skilled in the art, including synthetic (e.g., exclusive solid phase synthesis, partial solid phase synthesis, fragment condensation, classical solution synthesis, native-chemical ligation) and recombinant techniques. For example, the peptides or peptides derivatives can be obtained by solid phase peptide synthesis, which in brief, consist of coupling the carboxyl group of the C-terminal amino acid to a resin (e.g., benzhydrylamine resin, chloromethylated resin, hydroxymethyl resin) and successively adding N-alpha protected amino acids. The protecting groups may be any such groups known in the art. Before each new amino acid is added to the growing chain, the protecting group of the previous amino acid added to the chain is removed. Such solid phase synthesis has been disclosed, for example, by Merrifield, *J. Am. Chem. Soc.* 85: 2149 (1964); Vale et al., *Science* 213:1394-1397 (1981), in U.S. Pat. Nos. 4,305,872 and 4,316,891, Bodonsky et al. *Chem. Ind.* (London), 38:1597 (1966); and Pietta and Marshall, *Chem. Comm.* 650 (1970) by techniques reviewed in Lubell et al. "Peptides" Science of Synthesis 21.11, *Chemistry of Amides*. Thieme, Stuttgart, 713-809 (2005). The coupling of amino acids to appropriate resins is also well known in the art and has been disclosed in U.S. Pat. No. 4,244,946. (Reviewed in Houver-Weyl, *Methods of Organic Chemistry*. Vol E22a. Synthesis of Peptides and Peptidomimetics, Murray Goodman, Editor-in-Chief, Thieme. Stuttgart. New York 2002).

Unless defined otherwise, the scientific and technological terms and nomenclature used herein have the same meaning as commonly understood by a person of ordinary skill to which this invention pertains. Generally, the procedures of cell cultures, infection, molecular biology methods and the like are common methods used in the art. Such standard techniques can be found in reference manuals such as, for example, Ausubel et al., *Current Protocols in Molecular Biology*, Wiley Interscience, New York, 2001; and Sambrook et al., *Molecular Cloning: A Laboratory Manual*, 3$^{rd}$ edition, Cold Spring Harbor Laboratory Press, N.Y., 2001.

During any process of the preparation of an Ang-(1-7) peptide, it may be desirable to protect sensitive reactive groups on any of the molecule concerned. This may be achieved by means of conventional protecting groups such as those described in Protective Groups In Organic Synthesis by T. W. Greene & P. G. M. Wuts, 1991, John Wiley and Sons, New-York; and Peptides: chemistry and Biology by Sewald and Jakubke, 2002, Wiley-VCH, Wheinheim p. 142. For example, alpha amino protecting groups include acyl type protecting groups (e.g., trifluoroacetyl, formyl, acetyl), aliphatic urethane protecting groups (e.g., t-butyloxycarbonyl (BOC), cyclohexyloxycarbonyl), aromatic urethane type protecting groups (e.g., fluorenyl-9-methoxy-carbonyl (Fmoc), benzyloxycarbonyl (Cbz), Cbz derivatives) and alkyl type protecting groups (e.g., triphenyl methyl, benzyl). The amino acids side chain protecting groups include benzyl (for Thr and Ser), Cbz (Tyr, Thr, Ser, Arg, Lys), methyl ethyl, cyclohexyl (Asp, His), Boc (Arg, His, Cys) etc. The protecting groups may be removed at a convenient subsequent stage using methods known in the art.

Further, Ang-(1-7) peptides may be synthesized according to the FMOC protocol in an organic phase with protective groups. Desirably, the peptides are purified with a yield of 70% with high-pressure liquid chromatography (HPLC) on a C18 chromatography column and eluted with an acetonitrile gradient of 10-60%. The molecular weight of a peptide can be verified by mass spectrometry (reviewed in Fields, G. B. "Solid-Phase Peptide Synthesis" *Methods in Enzymology*. Vol. 289, Academic Press, 1997).

Alternatively, Ang-(1-7) peptides may be prepared in recombinant systems using, for example, polynucleotide sequences encoding the polypeptides. It is understood that a polypeptide may contain more than one of the above-described modifications within the same polypeptide.

While peptides may be effective in eliciting a biological activity in vitro, their effectiveness in vivo might be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Powell et al., *Pharm. Res.* 10:1268-1273 (1993)). In light of this, it is often advantageous to use modified versions of peptides. The modified peptides retain the structural characteristics of the original L-amino acid peptides that confer the desired biological activity of Ang-(1-7) but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable peptides. Thus, a peptide derivative or peptidomimetic of the present invention may be all L, all D or mixed D, L peptide, in either forward or reverse order. The presence of an N-terminal or C-terminal D-amino acid increases the in vivo stability of a peptide since peptidases cannot utilize a D-amino acid as a substrate (Powell et al., *Pharm. Res.* 10:1268-1273 (1993)). Reverse-D peptides are peptides containing D-amino acids, arranged in a reverse sequence relative to a peptide containing L-amino acids. Thus, the C-terminal residue of an L-amino acid peptide becomes N-terminal for the D-amino acid peptide, and so forth. Reverse D-peptides retain the same secondary conformation and therefore similar activity, as the L-amino acid peptides, but are more resistant to enzymatic degradation in vitro and in vivo, and thus can have greater therapeutic efficacy than the original peptide (Brady and Dodson, *Nature* 368:692-693 (1994); Jameson et al., *Nature* 368:744-746 (1994)). Similarly, a reverse-L peptide may be generated using standard methods where the C-terminus of the parent peptide becomes takes the place of the N-terminus of the reverse-L peptide. It is contemplated that reverse L-peptides of L-amino acid peptides that do not have significant secondary structure (e.g., short peptides) retain the same spacing and conformation of the side chains of the L-amino acid peptide and therefore often have the similar activity as the original L-amino acid peptide. Moreover, a reverse peptide may contain a combination of L- and D-amino acids. The spacing between amino acids and the conformation of the side chains may be retained resulting in similar activity as the original L-amino acid peptide.

Another effective approach to confer resistance to peptidases acting on the N-terminal or C-terminal residues of a peptide is to add chemical groups at the peptide termini, such that the modified peptide is no longer a substrate for the peptidase. One such chemical modification is glycosylation of the peptides at either or both termini. Certain chemical modifications, in particular N-terminal glycosylation, have been shown to increase the stability of peptides in human serum (Powell et al., *Pharm. Res.* 10:1268-1273 (1993)). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified peptides consisting of peptides bearing an N-terminal acetyl group and/or a C-terminal amide group.

Substitution of non-naturally-occurring amino acids for natural amino acids in a subsequence of the peptides can also confer resistance to proteolysis. Such a substitution can, for instance, confer resistance to proteolysis by exopeptidases acting on the N-terminus without affecting biological activity. Examples of non-naturally-occurring amino acids include $\alpha,\alpha$-disubstituted amino acids, N-alkyl amino acids, C-$\alpha$-methyl amino acids, $\beta$-amino acids, and $\beta$-methyl amino acids. Amino acids analogs useful in the present invention may include, but are not limited to, $\beta$-alanine, norvaline, norleucine, 4-aminobutyric acid, orithine, hydroxyproline, sarcosine, citrulline, cysteic acid, cyclo-hexylalanine, 2-aminoisobutyric acid, 6-aminohexanoic acid, t-butylglycine, phenylglycine, o-phosphoserine, N-acetyl serine, N-formylmethionine, 3-methylhistidine and other unconventional amino acids. Furthermore, the synthesis of peptides with non-naturally-occurring amino acids is routine in the art.

In addition, constrained peptides comprising a consensus sequence or a substantially identical consensus sequence variation may be generated by methods well known in the art (Rizo and Gierasch, *Ann. Rev. Biochem.* 61:387-418 (1992)). For example, constrained peptides may be generated by adding cysteine residues capable of forming disulfide bridges and, thereby, resulting in a cyclic peptide. Cyclic peptides can be constructed to have no free N- or C-termini. Accordingly, they are not susceptible to proteolysis by exopeptidases, although they may be susceptible to endopeptidases, which do not cleave at peptide termini. The amino acid sequences of the peptides with N-terminal or C-terminal D-amino acids and of the cyclic peptides are usually identical to the sequences of the peptides to which they correspond, except for the presence of N-terminal or C-terminal D-amino acid residue, or their circular structure, respectively.

Cyclic Peptides

In some embodiments, a functional equivalent, analogue or derivative of naturally-occurring Ang-(1-7) is a cyclic peptide. As used herein, a cyclic peptide has an intramolecular covalent bond between two non-adjacent residues. The intramolecular bond may be a backbone to backbone, side-chain to backbone or side-chain to side-chain bond (i.e., terminal functional groups of a linear peptide and/or side-chain functional groups of a terminal or interior residue may be linked to achieve cyclization). Typical intramolecular bonds include disulfide, amide and thioether bonds. A variety of means for cyclizing polypeptides are well known in the art, as are many other modifications that can be made to such peptides. For a general discussion, see International Patent Publication Nos. WO 01/53331 and WO 98/02452, the contents of which are incorporated herein by reference. Such cyclic bonds and other modifications can also be applied to the cyclic peptides and derivative compounds of this invention.

Cyclic peptides as described herein may comprise residues of L-amino acids, D-amino acids, or any combination thereof. Amino acids may be from natural or non-natural sources, provided that at least one amino group and at least one carboxyl group are present in the molecule; $\alpha$- and $\beta$-amino acids are generally preferred. Cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Suitable derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, $\beta,\beta$-tetramethylene cysteine, $\beta,\beta$-pentamethylene cysteine, $\beta$-mercaptopropionic acid, $\beta,\beta$-pentamethylene-$\beta$-mercaptopropionic acid, 2-mercaptobenzene, 2-mercaptoaniline, 2-mercaptoproline, ornithine, diaminobutyric acid, $\alpha$-aminoadipic acid, m-aminomethylbenzoic acid and $\alpha,\beta$-diaminopropionic acid.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Within further embodiments, cyclization may be achieved by amide bond formation. For example, a peptide bond may be formed between terminal functional groups (i.e., the amino and carboxy termini of a linear peptide prior to cyclization). Within another such embodiment, the linear peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), $\alpha$-amino adipic acid, m-aminomethylbenzoic acid, $\alpha,\beta$-diaminopropionic acid, glutamate or aspartate. Methods for forming amide bonds are generally well known in the art. Within one such method, carbodiimide-mediated lactam formation can be accomplished by reaction of the carboxylic acid with DCC, DIC, ED AC or DCCI, resulting in the formation of an O-acylurea that can be reacted immediately with the free amino group to complete the cyclization. Alternatively, cyclization can be performed using the azide method, in which a reactive azide intermediate is generated from an alkyl ester via a hydrazide. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF.

Exemplary Angiotensin-(1-7) Peptides

In certain aspects, the invention provides non-cyclic (e.g., linear) angiotensin-(1-7) peptides. As discussed above, the structure of naturally-occurring Ang-(1-7) is as follows:

(SEQ ID NO: 1)
$Asp^1$-$Arg^2$-$Val^3$-$Tyr^4$-$Ile^5$-$His^6$-$Pro^7$

The peptides and peptide analogs of the invention can be generally represented by the following sequence:

(SEQ ID NO: 5)
$Xaa^1$-$Xaa^2$-$Xaa^3$-$Xaa^4$-$Xaa^5$-$Xaa^6$-$Xaa^7$, or a pharmaceutically acceptable salt thereof.

$Xaa^1$ is any amino acid or a dicarboxylic acid. In certain embodiments, $Xaa^1$ is Asp, Glu, Asn, Acpc (1-aminocyclopentane carboxylic acid), Ala, $Me_2Gly$ (N,N-dimethylglycine), Pro, Bet (betaine, 1-carboxy-N,N,N-trimethylmethanaminium hydroxide), Glu, Gly, Asp, Sar (sarcosine) or Suc (succinic acid). In certain such embodiments, $Xaa^1$ is a negatively-charged amino acid, such as Asp or Glu, typically Asp.

$Xaa^2$ is Arg, Lys, Ala, Cit (citrulline), Orn (ornithine), acetylated Ser, Sar, D-Arg and D-Lys. In certain embodiments, $Xaa^2$ is a positively-charged amino acid such as Arg or Lys, typically Arg.

$Xaa^3$ is Val, Ala, Leu, Nle (norleucine), Ile, Gly, Lys, Pro, HydroxyPro (hydroxyproline), Aib (2-aminoisobutyric acid), Acpc or Tyr. In certain embodiments, $Xaa^3$ is an aliphatic amino acid such as Val, Leu, Ile or Nle, typically Val or Nle.

$Xaa^4$ is Tyr, Tyr($PO_3$), Thr, Ser, homoSer (homoserine), azaTyr (aza-$\alpha^1$-homo-L-tyrosine) or Ala. In certain embodiments, $Xaa^4$ is a hydroxyl-substituted amino acid such as Tyr, Ser or Thr, typically Tyr.

$Xaa^5$ is Ile, Ala, Leu, norLeu, Val or Gly. In certain embodiments, $Xaa^5$ is an aliphatic amino acid such as Val, Leu, Ile or Nle, typically Ile.

$Xaa^6$ is His, Arg or 6-$NH_2$-Phe (6-aminophenylalaine). In certain embodiments, $Xaa^6$ is a fully or partially positively-charged amino acid such as Arg or His.

$Xaa^7$ is Cys, Pro or Ala.

In certain embodiments, one or more of $Xaa^1$-$Xaa^7$ is identical to the corresponding amino acid in naturally-occurring Ang-(1-7). In certain such embodiments, all but one or two of $Xaa^1$-$Xaa^7$ are identical to the corresponding amino acid in naturally-occurring Ang-(1-7). In other embodiments, all of $Xaa^1$-$Xaa^6$ are identical to the corresponding amino acid in naturally-occurring Ang-(1-7).

In certain embodiments, $Xaa^3$ is Nle. When $Xaa^3$ is Nle, one or more of $Xaa^1$-$Xaa^2$ and $Xaa^{4-7}$ are optionally identical to the corresponding amino acid in naturally-occurring Ang-(1-7). In certain such embodiments, all but one or two of $Xaa^1$-$Xaa^2$ and $Xaa^{4-7}$ are identical to the corresponding amino acid in naturally-occurring Ang-(1-7). In other embodiments, all of $Xaa^1$-$Xaa^2$ and $Xaa^{4-7}$ are identical to the corresponding amino acid in naturally-occurring Ang-(1-7), resulting in the amino acid sequence: $Asp^1$-$Arg^2$-$Nle^3$-$Tyr^4$-$Ile^5$-$His^6$-$Pro^7$ (SEQ ID NO: 6).

In certain embodiments, the peptide has the amino acid sequence $Asp^1$-$Arg^2$-$Val^3$-$Ser^4$-$Ile^5$-$His^6$-$Cys^7$ (SEQ ID NO: 2) or $Ala^1$-$Arg^2$-$Val^3$-$Ser^4$-$Ile^5$-$His^6$-$Cys^7$ (SEQ ID NO: 3).

In some embodiments, a linear angiotensin (1-7) peptide as described herein is a peptide having a sequence of $Asp^1$-$Arg^2$-$Val^3$-$Tyr^4$-$Ile^5$-$His^6$-$Pro^7$-$Phe^8$-$His^9$ (SEQ ID NO: 22), which is identical to the sequence of Ang(1-9). In some embodiments, an angiotensin (1-7) peptide is a derivative of Ang (1-9). For exemplary Ang (1-9) peptides, including Ang(1-9) derivatives, see U.S. Patent Publication 2012/0172301, the disclosure of which is hereby incorporated by reference.

In some embodiments, a linear angiotensin (1-7) peptide is a peptide with an amino acid sequence of $Ala^1$-$Arg^2$-$Val^3$-$Tyr^4$-$Ile^5$-$His^6$-$Pro^7$ (SEQ ID NO: 23). Additional sequences derived from SEQ ID NO: 23 may be found in European Patent Application 2,264,048, the disclosure of which is hereby incorporated by reference.

Exemplary Cyclic Angiotensin (1-7) Peptides

In certain aspects, the invention provides a cyclic angiotensin-(1-7) (Ang-(1-7)) peptide analog comprising a linkage, such as between the side chains of amino acids corresponding to positions $Tyr^4$ and $Pro^7$ in Ang. These peptide analogs typically comprise 7 amino acid residues, but can also include a cleavable sequence. As discussed in greater detail below, the invention includes fragments and analogs where one or more amino acids are substituted by another amino acid (including fragments). One example of such an analog is $Asp^1$-$Arg^2$-$Val^3$-$Ser^4$-$Ile^5$-$His^6$-$Cys^7$ (SEQ ID NO: 2), wherein a linkage is formed between $Ser^4$ and $Cys^7$. Another example of such an analog is $Ala^1$-$Arg^2$-$Val^3$-$Ser^4$-$Ile^5$-$His^6$-$Cys^7$ (SEQ ID NO: 3), wherein a linkage is formed between $Ser^4$ and $Cys^7$. In some embodiments, a cyclic angiotensin (1-7) peptide analog is a cyclic analog that does not have a sequence according to SEQ ID NO: 1. In some embodiments, a cyclic angiotensin (1-7) peptide analog is a cyclic analog that does not have a sequence according to SEQ ID NO: 2. In some embodiments, a cyclic angiotensin (1-7) peptide analog is a cyclic analog that does not have a sequence according to SEQ ID NO: 3.

Although the following section describes aspects of the invention in terms of a thioether bond linking residues at the 4- and 7-positions, it should be understood that other linkages (as described above) could replace the thioether bridge and that other residues could be cyclized. A thioether bridge is also referred to as a monosulfide bridge or, in the case of Ala-S-Ala, as a lanthionine bridge. Thioether bridge-containing peptides can be formed by two amino acids having one of the following formulas:

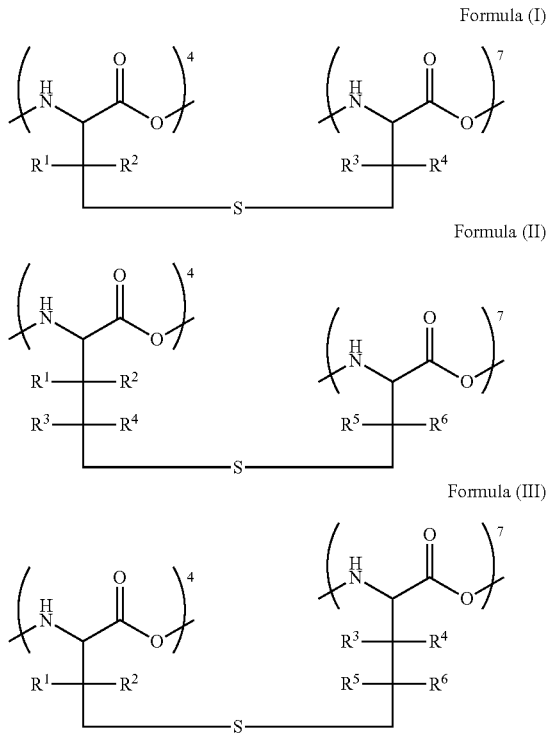

Formula (I)

Formula (II)

Formula (III)

In these formulae, $R^1$, $R^2$, $R^3$, $R^4$, $R^5$ and $R^6$ are independently —H, an alkyl (e.g., $C_1$-$C_6$ alkyl, $C_1$-$C_4$ alkyl) or an aralkyl group, where the alkyl and aralkyl groups are optionally substituted with one or more halogen, —OH or —NRR' groups (where R and R' are independently —H or $C_1$-$C_4$ alkyl). In certain embodiments, $R^1$, $R^2$, $R^3$, $R^4$, $R^5$ and $R^6$ are each independently —H or —$CH_3$, such where all are —H.

In certain embodiments, the invention provides an Ang analog or derivative comprising a thioether bridge according to formula (I). Typically, $R^1$, $R^2$, $R^3$ and $R^4$ are independently selected from —H and —$CH_3$. Peptides comprising a thioether bridge according to formula (I) can be produced, for example, by lantibiotic enzymes or by sulfur extrusion of a disulfide. In one example, the disulfide from which the sulfur is extruded can be formed by D-cysteine in position 4 and L-cysteine in position 7 or by D-cysteine in position 4 and L-penicillamine in position 7 (see, e.g., Galande, Trent and Spatola (2003) *Biopolymers* 71, 534-551).

In other embodiments, the linkage of the two amino acids can be the bridges depicted in Formula (II) or Formula (III). Peptides comprising a thioether bridge according to Formula (II) can be made, for example, by sulfur extrusion of a disulfide formed by D-homocysteine in position 4 and L-cysteine in position 7. Similarly, peptides comprising a thioether bridge as in Formula (III) can be made, for example, by sulfur extrusion of a disulfide formed by D-cysteine in position 4 and L-homocysteine in position 7.

As discussed above, the Ang analogs and derivatives of the invention vary in length and amino acid composition. The Ang analogs and derivatives of the invention preferably have biological activity or are an inactive precursor molecule that can be proteolytically activated (such as how angiotensin(I), with 10 amino acids, is converted to active fragments by cleavage of 2 amino acids). The size of an Ang analog or derivative can vary but is typically between from about 5 to 10 amino acids, as long as the "core" pentameric segment comprising the 3-7 Nle-thioether-ring structure is encompassed. The amino acid sequence of an analog or derivative of the invention can vary, typically provided that it is biologically active or can become proteolytically activated. Biological activity of an analog or derivative can be determined using methods known in the art, including radioligand binding studies, in vitro cell activation assays and in vivo experiments. See, for example, Godeny and Sayeski, (2006) *Am. J. Physiol. Cell. Physiol.* 291:C1297-1307; Sarr et al., *Cardiovasc. Res.* (2006) 71:794-802; and Koziarz et al., (1933) *Gen. Pharmacol.* 24:705-713.

Ang analogs and derivatives where only the length of the peptide is varied include the following:

a 4,7-cyclized analog designated [$Cyc^{4-7}$]Ang-(1-7), which is derived from natural Ang-(1-7) ($Asp^1$-$Arg^2$-$Val^3$-$Cyc^4$-$Ile^5$-$His^6$-$Cyc^7$, SEQ ID NO: 7).

a 4,7-cyclized analog designated [$Nle^3$, $Cyc^{4-7}$]Ang-(1-10), which is derived from natural Angiotensin I (Ang-(1-10)) ($Asp^1$-$Arg^2$-$Nle^3$-$Cyc^4$-$Ile^5$-$His^6$-$Cyc^7$-$Phe^8$-$His^9$-$Leu^{10}$, SEQ ID NO: 8);

a 4,7-cyclized analog designated [$Nle^3$, $Cyc^{4-7}$]Ang-(1-8), which is derived from natural Angiotensin II (Ang-(1-8)) ($Asp^1$-$Arg^2$-$Nle^3$-$Cyc^4$-$Ile^5$-$His^6$-$Cyc^7$-$Phe^8$, SEQ ID NO: 9);

a 4,7-cyclised analog designated [$Nle^3$, $Cyc^{4-7}$]Ang-(2-8), which is derived from natural Angiotensin III (Ang-(2-8)) ($Arg^2$-$Nle^3$-$Cyc^4$-$Ile^5$-$His^6$-$Cyc^7$-$Phe^8$, SEQ ID NO: 10);

a 4,7-cyclised analog designated [$Nle^3$, $Cyc^{4-7}$]Ang-(3-8), which is derived from natural Angiotensin IV (Ang-(3-8)) ($Nle^3$-$Cyc^4$-$Ile^5$-$His^6$-$Cyc^7$-$Phe^8$, SEQ ID NO: 11);

a 4,7-cyclised analog designated [$Nle^3$, $Cyc^{4-7}$]Ang-(1-7) derived from natural Ang-(1-7) ($Asp^1$-$Arg^2$-$Nle^3$-$Cyc^4$-$Ile^5$-$His^6$-$Cyc^7$, SEQ ID NO: 12); and a 4,7-cyclised analog designated [$Nle^3$, $Cyc^{4-7}$]Ang-(1-9) derived from natural Ang-(1-9) ($Asp^1$-$Arg^2$-$Nle^3$-$Cyc^4$-$Ile^5$-$His^6$-$Cyc^7$-$Phe^8$-$His^9$, SEQ ID NO: 13).

These analogs can have one of the thioether bridges shown in Formulae (I)-(III) as the $Cyc^{4-7}$ moiety, for example, where $Cyc^4$ and $Cyc^7$ are represented by Formula (I), such as where $R^1$-$R^4$ are each —H or —$CH_3$, typically —H.

As compared to the amino acid sequence of the natural angiotensin peptide, the amino acids at positions 4 and 7 of the $Cyc^{4-7}$ analog are modified to allow introduction of the thioether-ring structures shown above. In addition to the length of the Ang analogs, the amino acids at positions other than 3, 4 and 7 can be the same or different from the naturally-occurring peptide, typically provided that the analog retains a biological function. For analogs of inactive precursors, like [$Cyc^{4-7}$]Ang-(I-10), biological function refers to one or both of an analog's susceptibility to angiotensin-converting enzymes that can cleave it to a biologically active fragment (e.g. Ang-(I-8) or Ang-(I-7)) or the biological activity of the fragment itself. In certain embodiments, an Ang analog or derivative of the invention has no intrinsic function but inhibits the effects of one or more naturally-occurring angiotensin compounds.

In certain embodiments, an Ang analog of the invention is represented by Formula (IV):

(IV, SEQ ID NO: 14)
$Xaa^1$-$Xaa^2$-$Xaa^3$-$Cyc^4$-$Xaa^5$-$Xaa^6$-$Cyc^7$ $Xaa^1$ is any amino acid, but typically a negatively-charged amino acid such as Glu or Asp, more typically Asp.

$Xaa^2$ is a positively-charged amino acid such as Arg or Lys, typically Arg.

Xaa³ is an aliphatic amino acid, such as Leu, Ile or Val, typically Val.

Cyc⁴ forms a thioether bridge in conjunction with Cyc⁷. Cyc⁴ can be a D-stereoisomer and/or a L-stereoisomer, typically a D-stereoisomer. Examples of Cyc⁴ (taken with Cyc⁷) are shown in Formulas (I), (II) and (III). Typically, the R groups in Formulae (I), (II) and (III) are —H or —CH₃, especially —H.

Xaa⁵ is an aliphatic amino acid, such as Leu, Ile or Val, typically Ile.

Xaa⁶ is His.

Cyc⁷ forms a thioether bridge in conjunction with Cyc⁴, such as in Formula (I), (II) or (III). Cyc⁷ can be a D-stereoisomer and/or a L-stereoisomer, typically a L-stereoisomer. Examples of Cyc⁷ (taken with Cyc⁴) are shown in Formulas (I), (II), (III) and (IV). Typically, the R groups in Formulae (I), (II), and (III) and (IV) are —H or —CH₃, especially —H.

In certain embodiments, one or more of Xaa¹-Xaa⁶ (excluding Cyc⁴ and Cyc⁷) is identical to the corresponding amino acid in naturally-occurring Ang-(1-7). In certain such embodiments, all but one or two of Xaa¹-Xaa⁶ are identical to the corresponding amino acid in naturally-occurring Ang-(1-7). In other embodiments, all of Xaa¹-Xaa⁶ are identical to the corresponding amino acid in naturally-occurring Ang-(1-7).

In certain embodiments, Cyc⁴ and Cyc⁷ are independently selected from Abu (2-aminobutyric acid) and Ala (alanine), where Ala is present in at least one position. Thus, cyclic analogs can have a thioether linkage formed by -Ala⁴-S-Ala⁷-(Formula (I), where R¹-R⁴ are each —H); -Ala⁴-S-Abu⁷-(Formula (I): R¹-R³ are —H and R⁴ is —CH₃) or -Abu⁴-S-Ala⁷-(Formula (I): R¹, R³ and R⁴ are —H and R² is —CH₃). Specific examples of cyclic analogs comprise a -Abu⁴-S-Ala⁷- or -Ala⁴-S-Ala⁷-linkage.

In certain embodiments, the invention provides an Ang-(1-7) analog with a thioether-bridge between position 4 and position 7 having the amino acid sequence Asp¹-Arg²-Val³-Abu⁴-Ile⁵-His⁶-Ala⁷ (SEQ ID NO: 15) or the amino acid sequence Asp¹-Arg²-Val³-Ala⁴-Ile⁵-His⁶-Ala⁷ (SEQ ID NO: 16), which are represented by the following structural diagrams:

In certain embodiments, an Ang analog or derivative of the invention is represented by Formula (V):

Xaa¹-Xaa²-Nle³-Cyc⁴-Xaa⁵-Xaa⁶-Cyc⁷-Xaa⁸-Xaa⁹-Xaa¹⁰(V,SEQ ID NO: 17)

As discussed above, one or more of Xaa¹, Xaa², Xaa⁸, Xaa⁹ and Xaa¹⁰ are absent in certain embodiments. For example, (1) Xaa¹⁰ is absent, (2) Xaa⁹ and Xaa¹⁰ are absent, (3) Xaa⁸, Xaa⁹ and Xaa¹⁰ are absent, (4) Xaa¹ is absent, (5) Xaa¹ and Xaa¹⁰ are absent, (6) Xaa¹, Xaa⁹ and Xaa¹⁰ are absent, (7) Xaa¹, Xaa⁸, Xaa⁹ and Xaa¹⁰ are absent, (8) Xaa¹ and Xaa² are absent, (9) Xaa¹, Xaa² and Xaa¹⁰ are absent, (10) Xaa¹, Xaa², Xaa⁹ and Xaa¹⁰ are absent, or (11) Xaa¹, Xaa², Xaa⁸, Xaa⁹ and Xaa¹⁰ are absent. For each of these embodiments, the remaining amino acids have the values described below.

Xaa¹, when present, is any amino acid, but typically a negatively charged amino acid such as Glu or Asp, more typically Asp.

Xaa², when present, is a positively charged amino acid such as Arg or Lys, typically Arg.

Nle³ is norleucine.

Cyc⁴ forms a thioether bridge in conjunction with Cyc⁷. Cyc⁴ can be a D-stereoisomer and/or a L-stereoisomer, typically a D-stereoisomer. Examples of Cyc⁴ (taken with Cyc⁷) are shown in Formulas (I), (II) and (III). Typically, the R groups in Formulae (I), (II) and (III) are —H or —CH₃, especially —H.

Xaa⁵ is an aliphatic amino acid, such as Leu, Nle, Ile or Val, typically Ile.

Xaa⁶ is His.

Cyc⁷ forms a thioether bridge in conjunction with Cyc⁴, such as in Formula (I), (II) or (III). Cyc⁷ can be a D-stereoisomer and/or a L-stereoisomer, typically a L-stereoisomer. Examples of Cyc⁷ (taken with Cyc⁴) are shown in Formulas (I), (II) and (III). Typically, the R groups in Formulae (I), (II) and (III) are —H or —CH₃, especially —H.

Xaa⁸, when present, is an amino acid other than Pro, typically Phe or Ile. In certain embodiments, Ile results in an inhibitor of Ang(1-8). In certain embodiments, Phe maintains the biological activity of Ang(1-8) or Ang(1-10).

Xaa⁹, when present, is His.

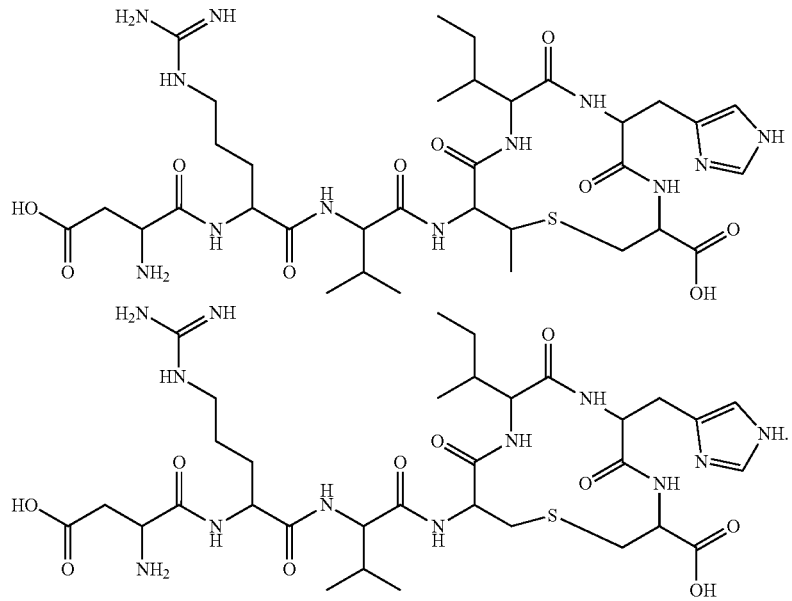

Xaa[10], when present, is an aliphatic residue, for example, Ile, Val or Leu, typically Leu.

In certain embodiments, one or more of Xaa[1]-Xaa[10] (excluding Nle[3], Cyc[4] and Cyc[7]) is identical to the corresponding amino acid in naturally-occurring Ang (including Ang-(1-7), Ang(1-8), Ang(1-9), Ang(1-10), Ang(2-7), Ang(2-8), Ang(2-9), Ang(2-10), Ang(3-8), Ang(3-9) and Ang(3-10). In certain such embodiments, all but one or two of Xaa[1]-Xaa[10] (for those present) are identical to the corresponding amino acid in naturally-occurring Ang. In other embodiments, all of Xaa[1]-Xaa[10] (for those present) are identical to the corresponding amino acid in naturally-occurring Ang.

In certain embodiments, Cyc[4] and Cyc[7] are independently selected from Abu (2-aminobutyric acid) and Ala (alanine), where Ala is present at least one position. Thus, encompassed are cyclic analogs comprising a thioether linkage formed by -Ala[4]-S-Ala[7]-(Formula (I), where $R^1$-$R^4$ are each —H); -Ala[4]-S-Abu[7]-(Formula (I): $R^1$-$R^3$ are —H and $R^4$ is —CH$_3$) or -Abu[4]-S-Ala[7]-(Formula (I): $R^1$, $R^3$ and $R^4$ are —H and $R^2$ is —CH$_3$). Specific cyclic analogs comprise a -Abu[4]-S-Ala[7]- or -Ala[4]-S-Ala[7]-linkage.

In particular, the invention provides an Ang-(I-7) analog or derivative with a thioether-bridge between position 4 and position 7 having the amino acid sequence Asp[1]-Arg[2]-Nle[3]-Abu[4]-Ile[5]-His[6]-Ala[7] (SEQ ID NO: 18) or the amino acid sequence Asp[1]-Arg[2]-Nle[3]-Ala[4]-Ile[5]-His[6]-Ala[7] (SEQ ID NO: 19).

In another aspect, the invention provides an Ang-(I-8) analog or derivative with a thioether-bridge between position 4 and position 7 having Ang-(I-8) antagonistic activity, in particular an Ang(I-8) analog or derivative having the amino acid sequence Asp[1]-Arg[2]-Nle[3]-Abu[4]-Ile[5]-His[6]-Ala[7]-Ile[8] (SEQ ID NO: 20), or the amino acid sequence Asp[1]-Arg[2]-Nle[3]-Ala[4]-Ile[5]-His[6]-Ala[7]-Ile[8] (SEQ ID NO: 21).

An alkyl group is a straight chained or branched non-aromatic hydrocarbon that is completely saturated. Typically, a straight chained or branched alkyl group has from 1 to about 20 carbon atoms, preferably from 1 to about 10. Examples of straight chained and branched alkyl groups include methyl, ethyl, n-propyl, iso-propyl, n-butyl, sec-butyl, tert-butyl, pentyl, hexyl, pentyl and octyl. A C1-C4 straight chained or branched alkyl group is also referred to as a "lower alkyl" group.

An aralkyl group is an alkyl group substituted by an aryl group. Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrrolyl, pyrazinyl, thiazolyl, oxazolyl, and tetrazolyl. Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

Ang (1-7) Receptor Agonists

In some embodiments, the present invention provides methods of treating epidermolysis bullosa including administering to a subject who is suffering from epidermolysis bullosa an angiotensin (1-7) receptor agonist. As used herein, the term "angiotensin-(1-7) receptor agonist" encompasses any molecule that has a positive impact in a function of an angiotensin-(1-7) receptor, in particular, the G-protein coupled Mas receptor. In some embodiments, an angiotensin-(1-7) receptor agonist directly or indirectly enhances, strengthens, activates and/or increases an angiotensin-(1-7) receptor (i.e., the Mas receptor) activity. In some embodiments, an angiotensin-(1-7) receptor agonist directly interacts with an angiotensin-(1-7) receptor (i.e., the Mas receptor). Such agonists can be peptidic or non-peptidic including, e.g., proteins, chemical compounds, small molecules, nucleic acids, antibodies, drugs, ligands, or other agents. In some embodiments, the angiotensin (1-7) receptor agonist is a non-peptidic agonist.

An exemplary class of angiotensin-(1-7) receptor agonists are 1-(p-thienylbenzyl)imidazoles. Examples of these non-peptide angiotensin-(1-7) receptor agonists are represented by Structural Formula (VI):

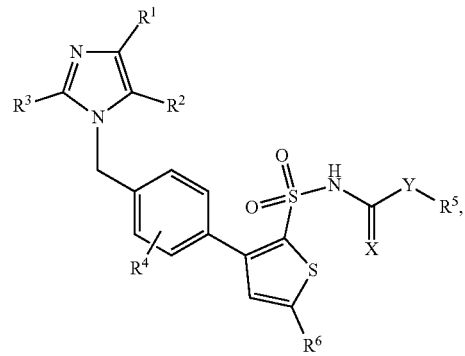

(VI)

or pharmaceutically acceptable salts thereof, wherein:

$R^1$ is halogen, hydroxyl, ($C_1$-$C_4$)-alkoxy, ($C_1$-$C_3$)-alkoxy wherein 1 to 6 carbon atoms are replaced by the heteroatoms O, S, or NH (preferably by O), ($C_1$-$C_4$)-alkoxy substituted by a saturated cyclic ether such as tetrahydropyran or tetrahydrofuran, O—($C_1$-$C_4$)-alkenyl, O—($C_1$-$C_4$)-alkylaryl, or aryloxy that is unsubstituted or substituted by a substituent selected from halogen, ($C_1$-$C_3$)-alkyl, ($C_1$-$C_3$)-alkoxy and trifluoromethyl;

$R^2$ is CHO, COOH, or (3) CO—O—($C_1$-$C_4$)-alkyl;

$R^3$ is ($C_1$-$C_4$)-alkyl or aryl;

$R^4$ is hydrogen, halogen (chloro, bromo, fluoro), or ($C_1$-$C_4$)-alkyl;

X is oxygen or sulfur;

Y is oxygen or —NH—;

$R^5$ is hydrogen, ($C_1$-$C_6$)-alkyl; or ($C_1$-$C_4$)-alkylaryl, where $R^5$ is hydrogen when Y is —NH—; and $R^6$ is ($C_1$-$C_5$)-alkyl.

In certain embodiments, $R^1$ is not halogen when $R^2$ is COOH or CO—O—($C_1$-$C_4$)-alkyl.

In some embodiments, an angiotensin-(1-7) receptor agonist is AVE 0991, 5-formyl-4-methoxy-2-phenyl-1[[4-[2-(ethylaminocarbonylsulfonamido)-5-isobutyl-3-thienyl]-phenyl]-methyl]-imidazole, which is represented by the following structure:

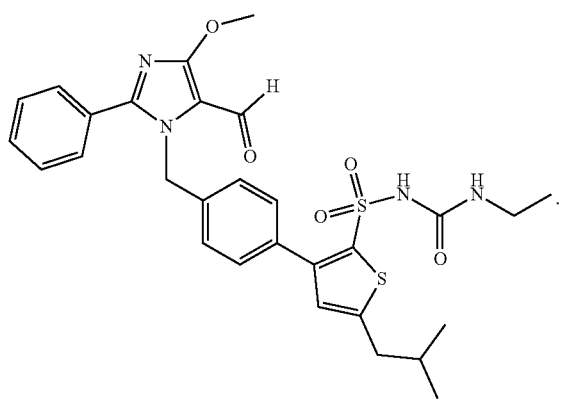 [SMILES: CCNC(=O)NS(=O)(=O)c1sc(CC(C)C)cc1-c1ccc(Cn2c(-c3ccccc3)nc(OC)c2C=O)cc1]

Another exemplary class of angiotensin-(1-7) receptor agonists are p-thienylbenzylamides. Examples of these non-peptide angiotensin-(1-7) receptor agonists are represented by Structural Formula (VII):

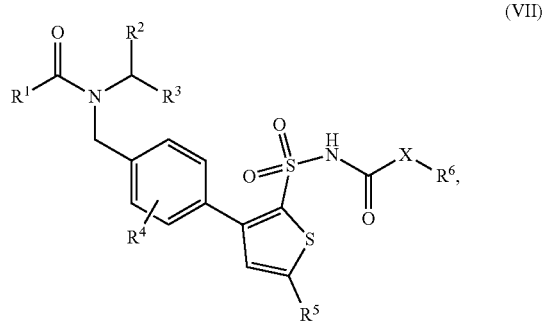

(VII)

or a pharmaceutically acceptable salt thereof, wherein:

$R^1$ is $(C_1-C_5)$-alkyl that is unsubstituted or substituted by a radical chosen from $NH_2$, halogen, O—$(C_1-C_3)$-alkyl, CO—O—$(C_1-C_3)$-alkyl and $CO_2H$, $(C_3-C_8)$-cycloalkyl, $(C_1-C_3)$-alkyl-$(C_3-C_8)$-cycloalkyl, $(C_6-C_{10})$-aryl that is unsubstituted or substituted by a radical chosen from halogen and O—$(C_1-C_3)$-alkyl, $(C_1-C_3)$-alkyl-$(C_6-C_{10})$-aryl where the aryl radical is unsubstituted or substituted by a radical chosen from halogen and O—$(C_1-C_3)$-alkyl, $(C_1-C_5)$-heteroaryl, or $(C_1-C_3)$-alkyl-$(C_1-C_5)$-heteroaryl;

$R^2$ is hydrogen, $(C_1-C_6)$-alkyl that is unsubstituted or substituted by a radical chosen from halogen and O—$(C_1-C_3)$-alkyl, $(C_3-C_8)$-cycloalkyl, $(C_1-C_3)$-alkyl-$(C_3-C_8)$-cycloalkyl, $(C_6-C_{10})$-aryl that is unsubstituted or substituted by a radical chosen from among halogen, O—$(C_1-C_3)$-alkyl and CO—O—$(C_1-C_3)$-alkyl, or $(C_1-C_3)$-alkyl-$(C_6-C_{10})$-aryl that is unsubstituted or substituted by a radical chosen from halogen and O—$(C_1-C_3)$-alkyl;

$R^3$ is hydrogen, COOH, or COO—$(C_1-C_4)$-alkyl;

$R^4$ is hydrogen, halogen; or $(C_1-C_4)$-alkyl;

$R^5$ is hydrogen or $(C_1-C_6)$-alkyl;

$R^6$ is hydrogen, $(C_1-C_6)$-alkyl, $(C_1-C_3)$-alkyl-$(C_3-C_3)$-cycloalkyl, or $(C_2-C_6)$-alkenyl; and X is oxygen or NH.

Additional examples of angiotensin-(1-7) receptor agonists are described in U.S. Pat. No. 6,235,766, the contents of which are incorporated by reference herein.

Various angiotensin-(1-7) receptor agonists described above can be present as pharmaceutically acceptable salts. As used herein, "a pharmaceutically acceptable salt" refers to salts that retain the desired activity of the peptide or equivalent compound, but preferably do not detrimentally affect the activity of the peptide or other component of a system, which uses the peptide. Examples of such salts are acid addition salts formed with inorganic acids, for example, hydrochloric acid, hydrobromic acid, sulfuric acid, phosphoric acid, nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts formed from a cationic material may utilize the conjugate base of these inorganic and organic acids. Salts may also be formed with polyvalent metal cations such as zinc, calcium, bismuth, barium, magnesium, aluminum, copper, cobalt, nickel and the like or with an organic cation formed from N,N'-dibenzylethylenediamine or ethylenediamine, or combinations thereof (e.g., a zinc tannate salt). The non-toxic, physiologically acceptable salts are preferred.

The salts can be formed by conventional means such as by reacting the free acid or free base forms of the product with one or more equivalents of the appropriate acid or base in a solvent or medium in which the salt is insoluble, or in a solvent such as water which is then removed in vacuo or by freeze-drying, or by exchanging the cations of an existing salt for another cation on a suitable ion exchange resin.

An alkyl group is a straight chained or branched non-aromatic hydrocarbon that is completely saturated. Typically, a straight chained or branched alkyl group has from 1 to about 20 carbon atoms, preferably from 1 to about 10. Examples of straight chained and branched alkyl groups include methyl, ethyl, n-propyl, iso-propyl, n-butyl, sec-butyl, tert-butyl, pentyl, hexyl, pentyl and octyl. A C1-C4 straight chained or branched alkyl group is also referred to as a "lower alkyl" group.

An alkenyl group is a straight chained or branched non-aromatic hydrocarbon that is includes one or more double bonds. Typically, a straight chained or branched alkenyl group has from 2 to about 20 carbon atoms, preferably from 2 to about 10. Examples of straight chained and branched alkenyl groups include ethenyl, n-propenyl, and n-butenyl.

Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrrolyl, pyrazinyl, thiazolyl, oxazolyl, and tetrazolyl. Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

An aralkyl group is an alkyl group substituted by an aryl group.

Formulations and Dosing

In accordance with the methods of the invention, an Ang (1-7) peptide or angiotensin (1-7) receptor agonist as described herein of the invention can be administered to a subject alone (e.g., as a purified peptide or compound), or as a component of a composition or medicament (e.g., in the manufacture of a medicament for the treatment of the disease), as described herein or otherwise known in the art. The compositions can be formulated with a physiologically acceptable carrier or excipient to prepare a pharmaceutical composition. The carrier and composition can be sterile. The formulation should suit the mode of administration, for example intravenous or subcutaneous administration. Methods of formulating compositions are known in the art (see, e.g., Remington's Pharmaceuticals Sciences, 17th Edition, Mack Publishing Co., (Alfonso R. Gennaro, editor) (1989)).

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring and/or aromatic substances and the like), which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, sustained release formulation, or powder. The composition can also be formulated as a suppository, with traditional binders and carriers such as triglycerides.

The composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

An Ang (1-7) peptide or angiotensin (1-7) receptor agonist as described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

An Ang (1-7) peptide or angiotensin (1-7) receptor agonist as described herein (or a composition or medicament containing an Ang (1-7) peptide or angiotensin (1-7) receptor agonist described herein) is administered by any appropriate route. In some embodiments, an Ang (1-7) peptide or angiotensin (1-7) receptor agonist described herein is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, an Ang (1-7) peptide or angiotensin (1-7) receptor agonist described herein is administered intravenously. Alternatively, an Ang (1-7) peptide or angiotensin (1-7) receptor agonist described herein (or a composition or medicament containing an Ang (1-7) peptide or angiotensin (1-7) receptor agonist described herein) can be administered by inhalation, parenterally, intradermally, transdermally, rectally, or transmucosally. In some embodiments, an Ang(1-7) peptide or angiotensin (1-7) receptor agonist is administered orally. More than one route can be used concurrently, if desired.

In some embodiments, a composition is administered in a therapeutically effective amount and/or according to a dosing regimen that is correlated with a particular desired outcome (e.g., with treating or reducing risk for epidermolysis bullosa).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100% or more. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100%. Alternatively or additionally, in some embodiments, an appropriate dose or amount is determined through use of one or more in vitro or in vivo assays to help identify desirable or optimal dosage ranges or amounts to be administered.

In various embodiments, an Ang (1-7) peptide or angiotensin (1-7) receptor agonist is administered at a therapeutically effective amount. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

Therapeutically effective dosage amounts of angiotensin (1-7) peptides or angiotensin (1-7) receptor agonists, including derivatives, analogs, and/or salts may be present in varying amounts in various embodiments. For example, in some embodiments, a therapeutically effective amount of an angiotensin (1-7) peptide may be an amount ranging from about 10-1,000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1,000 mg, 100-900 mg, 100-800 mg, 100-700 mg, 100-600 mg, 100-500 mg, 100-400 mg, 100-300 mg, 200-1,000 mg, 200-900 mg, 200-800 mg, 200-700 mg, 200-600 mg, 200-500 mg, 200-400 mg, 300-1,000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, an angiotensin (1-7) peptide or angiotensin (1-7) receptor agonist is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, an angiotensin (1-7) peptide or angiotensin (1-7) receptor agonist is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg. In some embodiments, the therapeutically effective amount described herein is provided in one dose. In some embodiments, the therapeutically effective amount described herein is provided in one day.

In other embodiments, a therapeutically effective dosage amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.001 mg/kg weight to about 1 mg/kg weight, e.g. from about 0.001 mg/kg weight to about 0.9 mg/kg weight, from about 0.001 mg/kg weight to about 0.8 mg/kg weight, from about 0.001 mg/kg weight to about 0.8 mg/kg weight, from about 0.001 mg/kg weight to about 0.7 mg/kg weight, from about 0.001 mg/kg weight to about 0.6 mg/kg weight, from about 0.001 mg/kg weight to about 0.5 mg/kg weight, from about 0.01 mg/kg weight to about 1 mg/kg weight, from about 0.01 mg/kg weight to about 0.9 mg/kg weight, from about 0.01 mg/kg weight to about 0.8 mg/kg weight, from about 0.01 mg/kg weight to about 0.7 mg/kg weight, from about 0.01 mg/kg weight to about 0.6 mg/kg weight, from about 0.01 mg/kg weight to about 0.5 mg/kg weight, from about 0.02 mg/kg weight to about 1 mg/kg weight, from about 0.02 mg/kg weight to about 0.9 mg/kg weight, from about 0.02 mg/kg weight to about 0.8 mg/kg weight, from about 0.02 mg/kg weight to about 0.7 mg/kg weight, from about 0.02 mg/kg weight to about 0.6 mg/kg weight, from about 0.02 mg/kg weight to about 0.5 mg/kg weight, from about 0.03 mg/kg weight to about 1 mg/kg weight, from about 0.03 mg/kg weight to about 0.9 mg/kg weight, from about 0.03 mg/kg weight to about 0.8 mg/kg weight, from about 0.03 mg/kg weight to about 0.7 mg/kg weight, from about 0.03 mg/kg weight to about 0.6 mg/kg weight, from about 0.03 mg/kg weight to about 0.5 mg/kg weight, from about 0.04 mg/kg weight to about 1 mg/kg weight, from about 0.04 mg/kg weight to about 0.9 mg/kg weight, from about 0.04 mg/kg weight to about 0.8 mg/kg weight, from about 0.04 mg/kg weight to about 0.7 mg/kg weight, from about 0.04 mg/kg weight to about 0.6 mg/kg weight, from about 0.04 mg/kg weight to about 0.5 mg/kg weight, from about 0.05 mg/kg weight to about 1 mg/kg weight, from about 0.05 mg/kg weight to about 0.9 mg/kg weight, from about 0.05 mg/kg weight to about 0.8 mg/kg weight, from about 0.05 mg/kg weight to about 0.7 mg/kg weight, from about 0.05 mg/kg weight to about 0.6 mg/kg weight, from about 0.05 mg/kg weight to about 0.5 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, the angiotensin (1-7) peptide is administered at an effective dose ranging from about 1-1,000 μg/kg/day (e.g., ranging from about 1-900 μg/kg/day, 1-800 μg/kg/day, 1-700 μg/kg/day, 1-600 μg/kg/day, 1-500 μg/kg/day, 1-400 μg/kg/day, 1-300 μg/kg/day, 1-200 μg/kg/day, 1-100 μg/kg/day, 1-90 μg/kg/day, 1-80 μg/kg/day, 1-70 μg/kg/day, 1-60 μg/kg/day, 1-50 μg/kg/day, 1-40 μg/kg/day, 1-30 μg/kg/day, 1-20 μg/kg/day, 1-10 μg/kg/day). In some embodiments, the angiotensin (1-7) peptide is administered at an effective dose ranging from about 1-500 µg/kg/day. In some embodiments, the angiotensin (1-7) peptide is administered at an effective dose ranging from about 1-100 µg/kg/day. In some embodiments, the angiotensin (1-7) peptide is administered at an effective dose ranging from about 1-60 µg/kg/day. In some embodiments, the angiotensin (1-7) peptide is administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 µg/kg/day.

Combination Therapies

In some embodiments, an Ang (1-7) peptide or an angiotensin (1-7) receptor agonist will be used as a part of a combination therapy. In some embodiments, an Ang(1-7) peptide and/or an angiotensin (1-7) receptor agonist may be administered prior to, concurrently with, or subsequent to one or more additional therapies. It is contemplated that any known therapy or therapeutic for the treatment of epidermolysis bullosa may be used with one or more Ang (1-7) peptides and/or angiotensin (1-7) receptor agonists as disclosed herein. Exemplary therapies that may be used with one or more Ang (1-7) peptides or angiotensin (1-7) receptor agonists include, but are not limited to, medications that can help control pain and itching, medications that address complications such as sepsis (e.g., antibiotics), medications that reduce inflammation (e.g., corticosteroid), surgery to correct abnormal motion (e.g., surgery to correct fusing of finger or toes or abnormal bends in the joints), surgery to improve the ability to eat a healthy diet (e.g., surgical dilation of the esophagus or placement of a feeding tube), skin grafts (e.g., OrCel composite cultured skin), gene therapy, bone marrow transplantation, protein replacement therapy, cell-based therapies, and/or combinations thereof, among others.

Kits

In some embodiments, the present invention further provides kits or other articles of manufacture which contains an Ang (1-7) peptide, an angiotensin (1-7) receptor agonist or a formulation containing the same and provides instructions for its reconstitution (if lyophilized) and/or use. Kits or other articles of manufacture may include a container, a syringe, vial and any other articles, devices or equipment useful in administration (e.g., subcutaneous, by inhalation). Suitable containers include, for example, bottles, vials, syringes (e.g., pre-filled syringes), ampules, cartridges, reservoirs, or lyojects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may hold one or more formulations and a label on, or associated with, the container that may indicate directions for reconstitution and/or use. For example, the label may indicate that the formulation is reconstituted to concentrations as described above. The label may further indicate that the formulation is useful or intended for, for example, subcutaneous administration. In some embodiments, a container may contain a single dose of a stable formulation containing an Ang (1-7) peptide or angiotensin (1-7) receptor agonist. In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 20 mg/ml, at least 30 mg/ml, at least 40 mg/ml, at least 50 mg/ml, at least 75 mg/ml, at least 100 mg/ml). Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for self-administration.

EXEMPLIFICATION

While certain compositions and methods of the present invention have been described with specificity in accordance with certain embodiments, the following example serves only to illustrate the compounds and methods of the invention, and it is not intended to limit the same.

Example 1. Angiotensin (1-7) Alleviates Fibrosis in a Mouse Model of Epidermolysis Bullosa Recessive dystrophic epidermolysis bullosa (RDEB) is caused by a mutation in the gene encoding type VII collagen. RDEB mice display marked fibrosis, which leads to deleterious phenotypes including the fibrosis-driven loss and fusion of digits over time (see, e.g., Nyström, A. et al., EMBO MOLECULAR MEDICINE 7(9):1211-28 (2015)).

Figure 2:
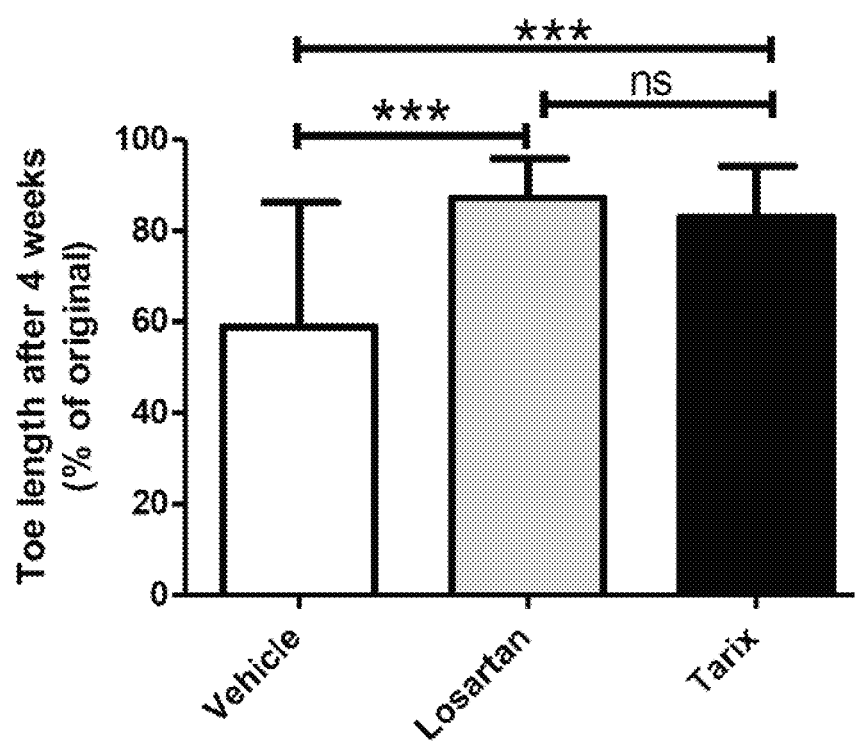
FIG. 2 is a graph of average toe length of recessive dystrophic epidermolysis bullosa (RDEB) mice treated with either angiotensin (1-7) peptide, losartan, or a vehicle control for four weeks as a percentage of average toe length before treatment. Angiotensin (1-7) treatment resulted in a significant reduction in the decrease in toe length relative to vehicle-treated RDEB controls. Results observed with angiotensin (1-7) were similar to those observed with losartan.

RDEB mice were treated with angiotensin (1-7) for four weeks (nine mice) or left untreated (three mice). Three wild type mice served as controls. Angiotensin (1-7) protected against RDEB-associated decreases in toe length and fusion of digits relative to results published by Nyström, A. et al. (EMBO MOLECULAR MEDICINE 7(9):1211-28 (2015)) (FIGS. 1A-1B). In particular, angiotensin (1-7) displayed similar efficacy as the angiotensin II receptor antagonist losartan as assessed by comparison with results published by Nyström, A. et al. (FIG. 2).

Figure 3:
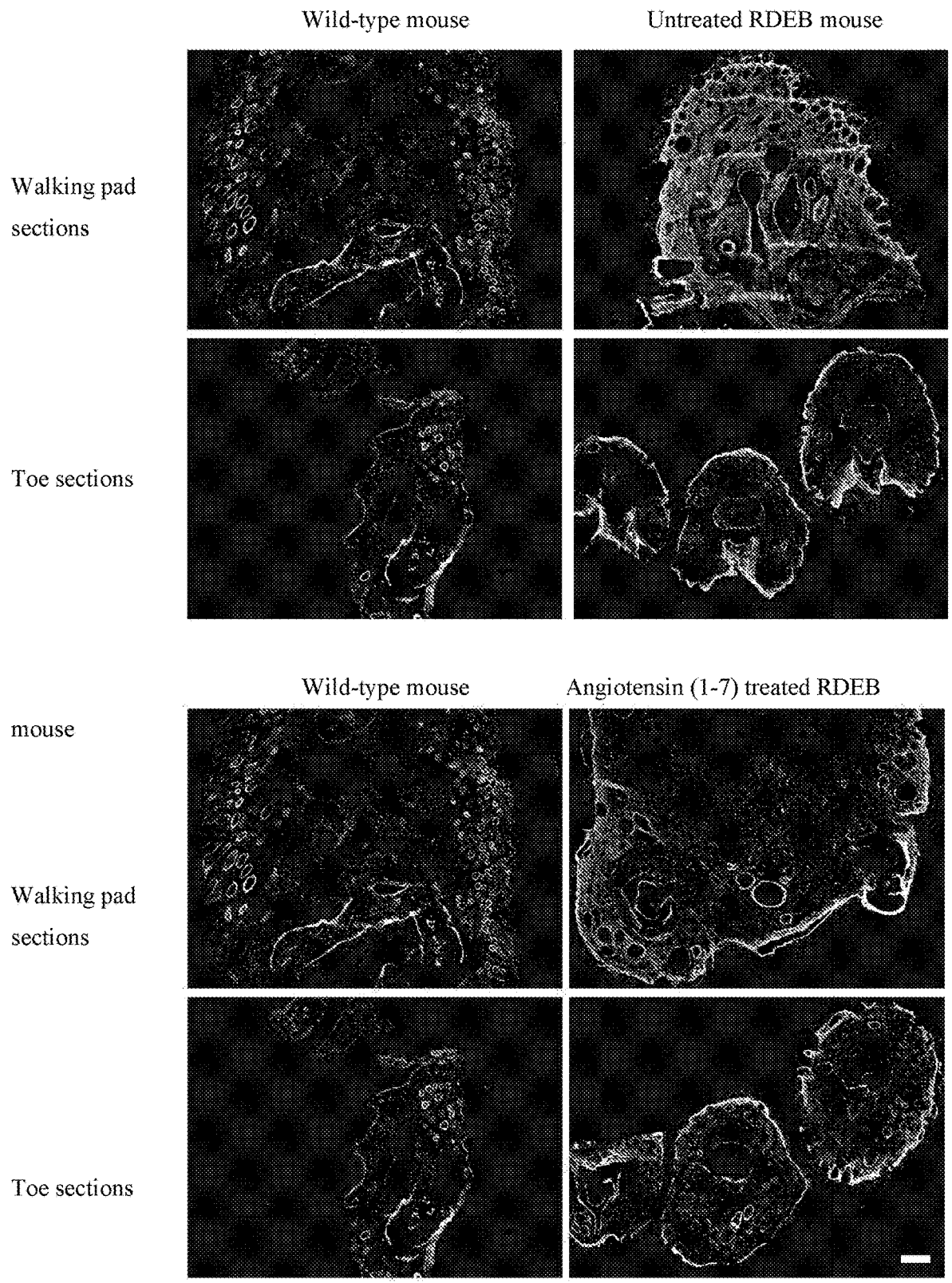
FIG. 3 depicts images of tenascin-C immunostained cryosections of mouse forepaws. The cryosections were obtained from age-matched wild-type mice, untreated recessive dystrophic epidermolysis bullosa (RDEB) mice, and RDEB mice treated with angiotensin (1-7) for four weeks. Each top panel corresponds to cryosections of the walking pads of a mouse, and each bottom panel corresponds to sections of toes. Tenascin-C is present at low abundance in uninjured skin, and it increases in fibrotic skin. The immunostained images show that tenascin-C is abundant in the untreated RDEB mouse forepaw dermis. Angiotensin (1-7) treatment significantly lowered the amount of tenascin-C staining. Tenascin-C staining was observed primarily just below the dermal-epidermal junction in angiotensin (1-7) treated mice, which corresponds to the initial site of injury in RDEB mice. Cells were counterstained with 4',6-diamidino-2-phenylindole (DAPI), and the scale bar corresponds to 200 µm.

Immunostaining was performed on cryosections of mouse forepaws of wild-type mice, untreated RDEB mice, and RDEB mice treated with angiotensin (1-7) for four weeks. Tenascin-C is present at low abundance in uninjured skin, but it increases in fibrotic skin. Tenascin-C immunostaining was visualized using fluorescence microscopy (FIG. 3). Immunostaining was quantified with ImageJ software on images obtained with identical microscope settings and exposure time. Each permutation of two groups was paired, and Student's paired t-test was used for statistical analysis.

Figure 4:
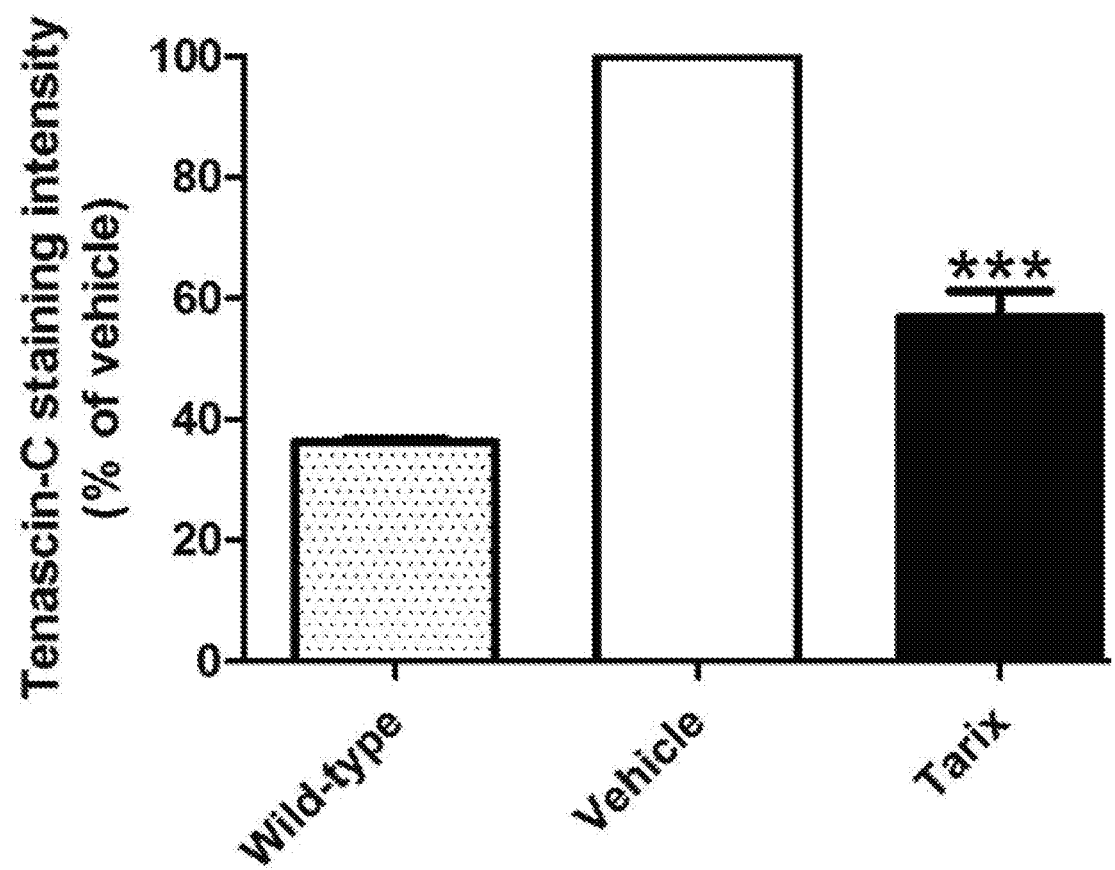
FIG. 4 is a graph depicting the quantification of the fluorescence intensity of cryosection images of mouse forepaws immunostained with an anti-tenascin-C antibody. The cryosections were obtained from age-matched wild-type mice, untreated recessive dystrophic epidermolysis bullosa (RDEB) mice, and RDEB mice treated with angiotensin (1-7) for four weeks. Each bar corresponds to a mean value, and error bars correspond to standard error of the mean (SEM). Mice treated with angiotensin (1-7) displayed a significant reduction in tenascin-C immunostaining relative to untreated controls (*** $P<0.001$).

Tenascin-C immunostaining was mostly absent in wild-type mice, but tenascin-C immunostaining was abundant in the untreated RDEB mouse forepaw dermis (FIGS. 3 & 4). Tenascin-C staining was observed primarily just below the dermal-epidermal junction in angiotensin (1-7) treated mice, which corresponds to the initial site of injury in RDEB mice (FIG. 3). Mice treated with angiotensin (1-7) displayed a significant ($P<0.001$) reduction in tenascin-C staining relative to untreated controls (FIG. 4). These results suggest that angiotensin (1-7) slows epidermolysis bullosa disease progression.

Cryosections of mouse forepaws were also immunostained for α-SMA (alpha smooth muscle actin), fibronectin, and CD11b. α-SMA is a myofibroblast cell marker, which correlates with fibrotic disease. Fibronectin correlates with dermal fibrosis. CD11b (integrin αM subunit) is a leukocyte marker, which is expressed by monocytes, granulocytes (e.g., neutrophils), macrophages, and natural killer cells. The presence of CD11b-positive cells in forepaw dermis suggests that the cells are inflammatory leukocytes (e.g., neutrophils and macrophages), which correlate with fibrotic disease.

Figure 5:
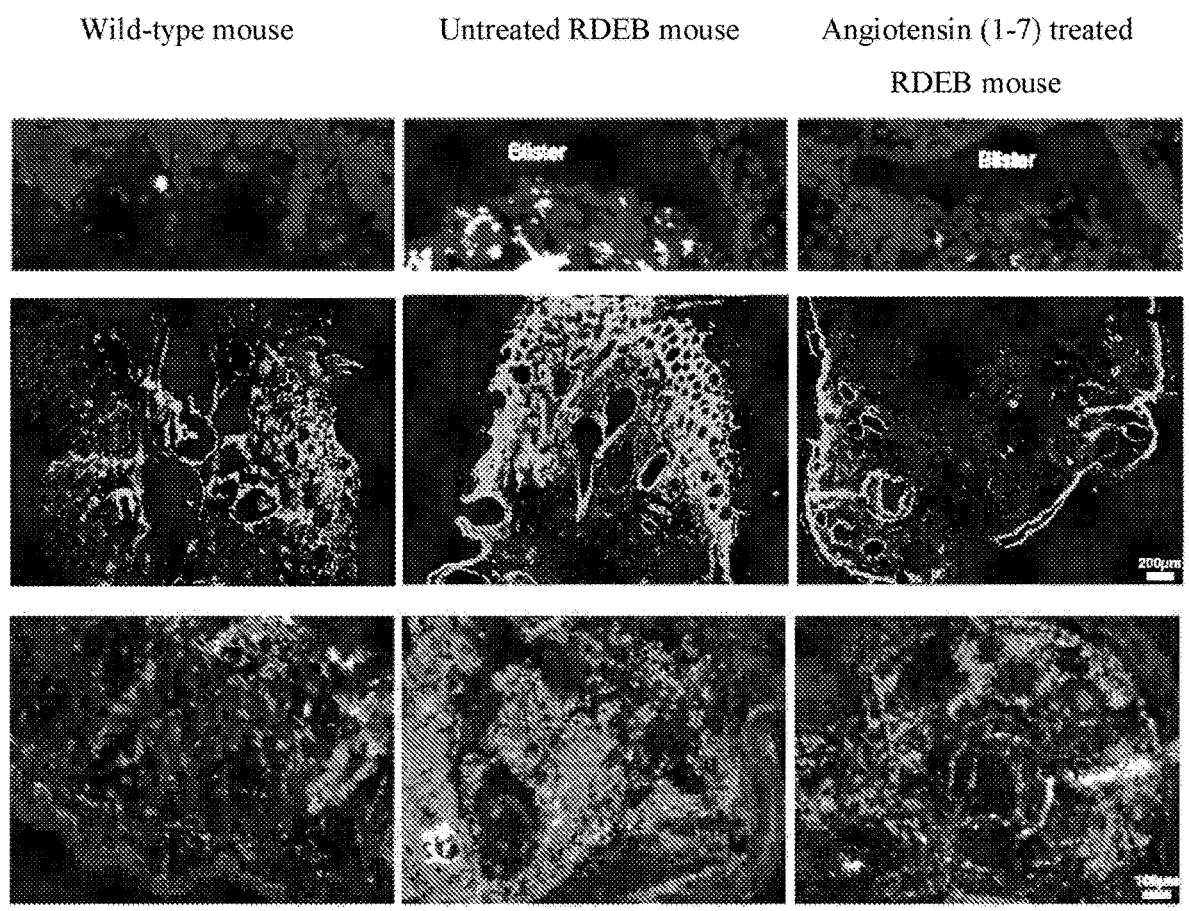
FIG. 5 depicts images of α-SMA (top panel), fibronectin (middle panel), and CD11b (bottom panel) immunostained cryosections of mouse forepaws. The cryosections were obtained from age-matched wild-type mice, untreated recessive dystrophic epidermolysis bullosa (RDEB) mice, and RDEB mice treated with angiotensin (1-7) for four weeks. Angiotensin (1-7) treatment reduced the number of α-SMA positive myofibroblasts, dermal fibronectin expression (which is indicative of dermal fibrosis), and CD11b-positive inflammatory leukocytes (neutrophils and macrophages) in RDEB mouse forepaw dermis. Cells were counterstained with 4',6-diamidino-2-phenylindole (DAPI).

RDEB is associated with blistering, and the mouse forepaws of both angiotensin (1-7)-treated and untreated RDEB mice displayed blistering whereas age-matched wild type controls lacked blistering. The blisters of angiotensin (1-7)-treated mice displayed fewer α-SMA positive cells relative to untreated RDEB mice (FIG. 5, top panel). This result suggests that angiotensin (1-7) reduces myofibroblast-mediated fibrosis associated with blistering in RDEB animals.

RDEB mice treated with angiotensin (1-7) displayed less fibronectin immunostaining than untreated RDEB mice, suggesting that angiotensin (1-7) reduces fibrosis in RDEB animals (FIG. 5, middle panel).

Figure 6:
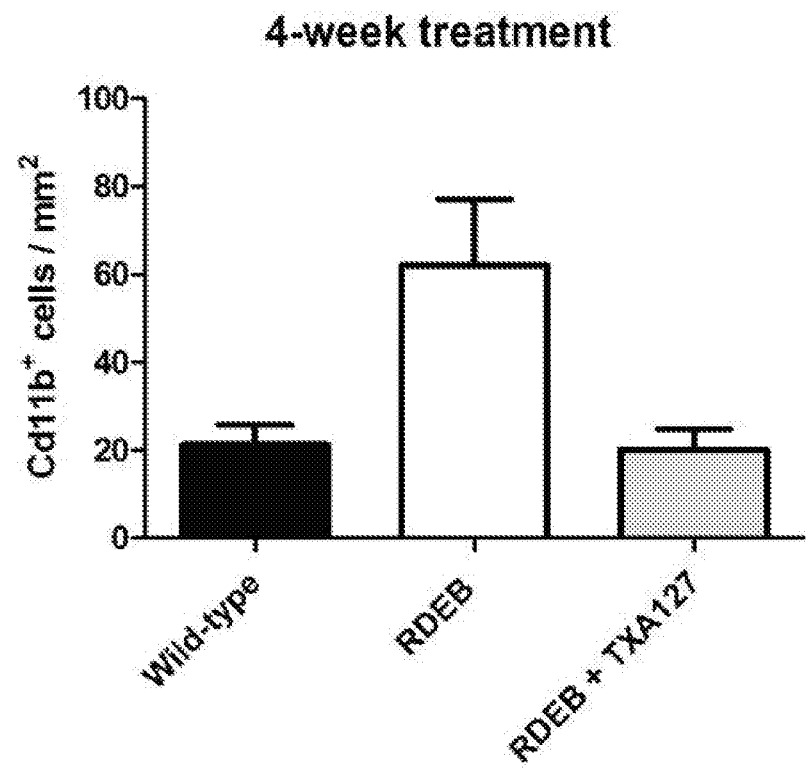
FIG. 6 is a graph depicting the quantification of CD11b-positive cells per $mm^2$ in images of immunostained cryosections of mouse forepaws. The cryosections were obtained from age-matched wild-type mice, untreated recessive dystrophic epidermolysis bullosa (RDEB) mice, and RDEB mice treated with angiotensin (1-7) for four weeks. CD11b stains neutrophils and macrophages. Mice treated with angiotensin (1-7) displayed a reduction in CD11b-positive cell density relative to untreated controls. Each bar corresponds to a mean value, and error bars correspond to standard error of the mean (SEM).

RDEB mice treated with angiotensin (1-7) displayed fewer CD11b-positive cells than untreated RDEB mice, suggesting that angiotensin (1-7) reduces leukocyte-mediated fibrosis in RDEB animals (FIG. 5, bottom panel). The number of CD11b-positive cells per $mm^2$ was quantified using ImageJ software. Briefly, images for wild type, untreated RDEB, and angiotensin (1-7)-treated RDEB mouse forepaw cryosections were acquired using identical microscope settings and exposure time. Identical thresholds were applied to all images, the images were converted to binary images, and all particles >10 pixles$^2$ were automatically counted. RDEB mice treated with angiotensin (1-7) displayed about the same number of CD11b-positive cells per $mm^2$ as wild type mice, whereas untreated RDEB mice displayed a ~3-fold increase in CD11b-positive cells (FIG. 6).

Figure 7:
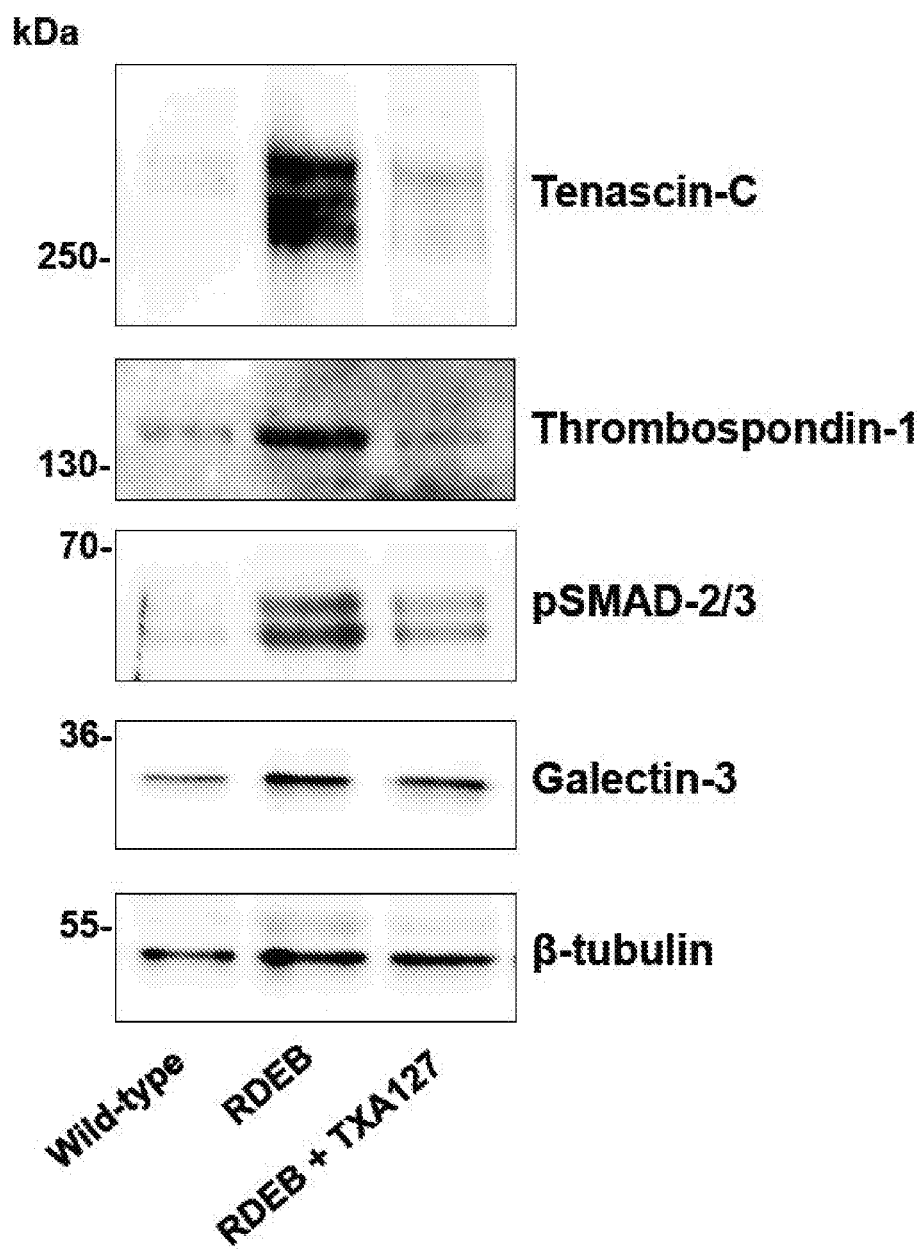
FIG. 7 depicts tenascin-C, thrombospondin-1, pSMAD2/3, galectin 3, and β-tubulin Western blots of whole protein lysates of mouse forepaws. Samples were obtained from age-matched wild-type mice, untreated recessive dystrophic epidermolysis bullosa (RDEB) mice, and RDEB mice treated with angiotensin (1-7) for four weeks. Mice treated with angiotensin (1-7) displayed reduced tenascin-C relative to untreated controls, which suggests that angiotensin (1-7) reduced dermal fibrosis. Mice treated with angiotensin (1-7) displayed a reduced abundance of the TGFβ activator thrombospondin-1 and a reduced abundance of phosphorylated SMAD2/3 (pSMAD2/3) relative to untreated controls, which suggest that angiotensin (1-7) downmodulated TGFβ-mediated signaling. Mice treated with angiotensin (1-7) displayed reduced galectin-3 relative to untreated controls, which suggests that angiotensin (1-7) alleviated pro-fibrotic inflammation.

Whole protein lysates from mouse forepaws were analyzed by Western blotting with antibodies directed against tenascin-C, thrombospondin-1, pSMAD2/3, galectin 3, and β-tubulin (FIG. 7). Thrombospondin 1 can activate transforming growth factor beta (TGFβ) signaling, which is associated with fibrosis. TGFβ signals through an intracellular SMAD pathway, and thus, phosphorylated-SMAD (e.g., pSMAD2/3) correlates with TGFβ-associated fibrosis. Galectin-3 expression correlates with pro-fibrotic inflammation. Western blotting results were quantified by densitometry and normalized against β-tubulin.

Figure 8:
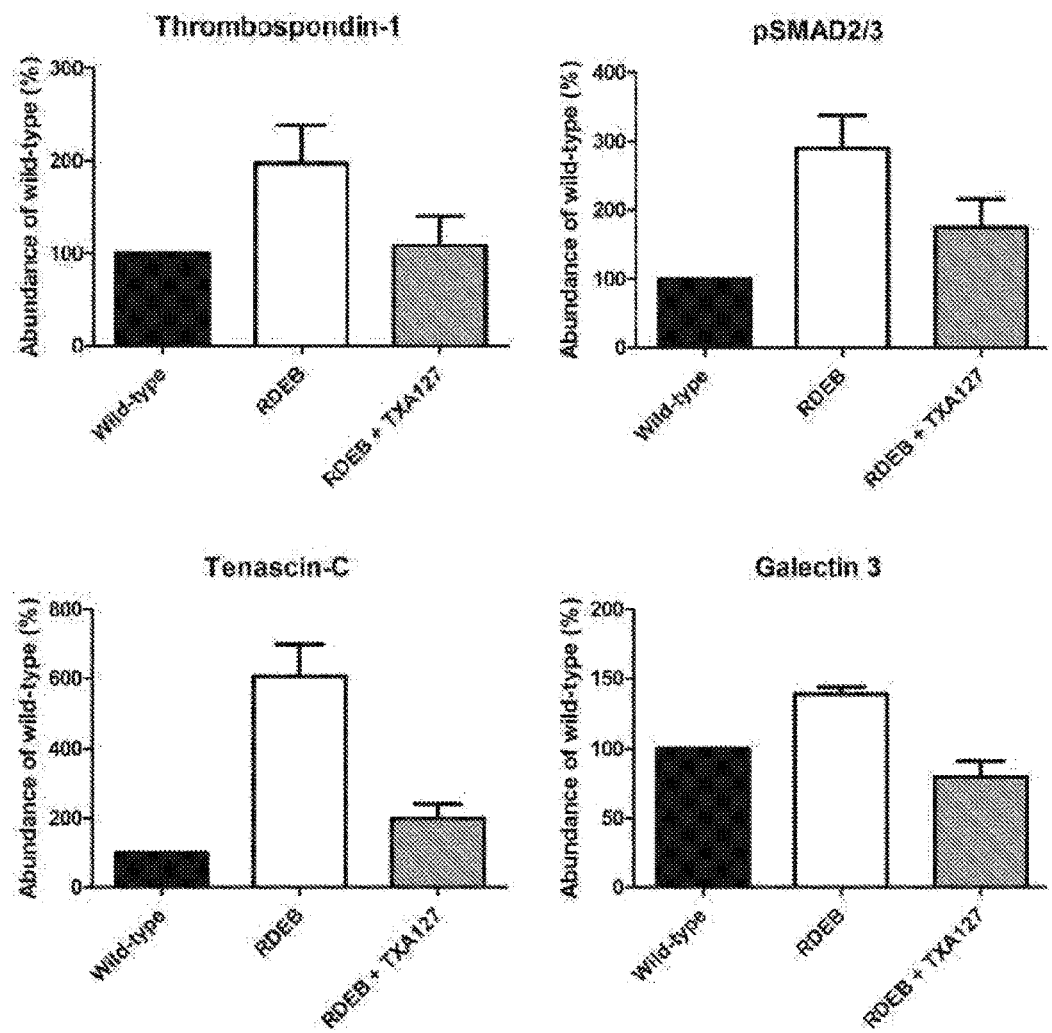
FIG. 8 is a graph depicting the quantification of Western blot bands immunostained with antibodies directed against tenascin-C, thrombospondin-1, pSMAD2/3, and galectin 3. Samples consisted of whole protein lysates of mouse forepaws obtained from age-matched wild-type mice, untreated recessive dystrophic epidermolysis bullosa (RDEB) mice, and RDEB mice treated with angiotensin (1-7) for four weeks. Samples were normalized against β-tubulin. Mice treated with angiotensin (1-7) displayed reduced tenascin-C, which suggests that angiotensin (1-7) reduced dermal fibrosis. Mice treated with angiotensin (1-7) displayed a reduced abundance of the TGFβ activator thrombospondin-1 and a reduced abundance of phosphorylated SMAD2/3 (pS-MAD2/3) relative to untreated controls, which suggest that angiotensin (1-7) downmodulated TGFβ activity. Mice treated with angiotensin (1-7) displayed reduced galectin-3, which suggests that angiotensin (1-7) alleviated pro-fibrotic inflammation. Each bar corresponds to a mean value, and error bars correspond to standard error of the mean (SEM).

RDEB mice treated with angiotensin (1-7) displayed reduced tenascin-C relative to untreated RDEB mice, which suggests that angiotensin (1-7) reduced dermal fibrosis (FIGS. 7 & 8). RDEB mice treated with angiotensin (1-7) displayed reduced abundance of the TGFβ activator thrombospondin-1 and reduced abundance of phosphorylated SMAD2/3 (pSMAD2/3) relative to untreated RDEB mice (FIGS. 7 & 8). This result suggests that angiotensin (1-7) downmodulated TGFβ activity. RDEB mice treated with angiotensin (1-7) displayed reduced galectin-3 relative to untreated RDEB mice, which suggests that angiotensin (1-7) alleviated pro-fibrotic inflammation (FIGS. 7 & 8).

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

I claim:

1. A method of treating epidermolysis bullosa comprising administering to a subject suffering from an epidermolysis bullosa an angiotensin (1-7) peptide.

2. The method of claim 1, wherein the administration is parenteral, rectal, oral, or a combination thereof.

3. The method of claim 2, wherein the parenteral administration is intravenous, subcutaneous, inhalation, intradermal, transdermal, and/or transmucosal administration.

4. The method of claim 1, wherein the epidermolysis bullosa is one or more of epidermolysis bullosa simplex (EBS), junctional epidermolysis bullosa (JEB), dystrophic epidermolysis bullosa (DEB), epidermolysis bullosa acquisita (EBA), and combinations thereof.

5. The method of claim 1, wherein the angiotensin (1-7) peptide is administered at an effective dose periodically at an administration interval such that at least one symptom or feature of one or more complications of epidermolysis bullosa is reduced in intensity, severity, duration, or frequency or has delayed onset.

6. The method of claim 5, wherein the one or more complications of epidermolysis bullosa is abnormal motion.

7. The method of claim 5, wherein the one or more complications of epidermolysis bullosa is infection.

8. The method of claim 5, wherein the one or more complications of epidermolysis bullosa is sepsis.

9. The method of claim 5, wherein the one or more complications of epidermolysis bullosa is deformities.

10. The method of claim 5, wherein the one or more complications of epidermolysis bullosa is malnutrition.

11. The method of claim 5, wherein the one or more complications of epidermolysis bullosa is anemia.

12. The method of claim 5, wherein the one or more complications of epidermolysis bullosa is dehydration.

13. The method of claim 5, wherein the one or more complications of epidermolysis bullosa is constipation.

14. The method of claim 5, wherein the one or more complications of epidermolysis bullosa is eye disorders.

15. The method of claim 5, wherein the one or more complications of epidermolysis bullosa is skin cancer.

16. The method of claim 1, wherein the angiotensin (1-7) peptide is administered once per day.

17. The method of any claim 1, wherein the angiotensin (1-7) peptide is administered at an effective dose ranging from about 50-500 μg/kg/day.

18. The method of claim 1, wherein the angiotensin (1-7) peptide is administered at an effective dose ranging from about 1-60 μg/kg/day.

19. The method of claim 1, wherein the angiotensin (1-7) peptide comprises the naturally-occurring Angiotensin (1-7) amino acid sequence of $Asp^1$-$Arg^2$-$Val^3$-$Tyr^4$-$Ile^5$-$His^6$-$Pro^7$ (SEQ ID NO: 1).

20. The method of claim 1, wherein the angiotensin (1-7) peptide comprises one or more chemical modifications to increase protease resistance, serum stability and/or bioavailability.

21. The method of claim 20, wherein the one or more chemical modifications comprise pegylation.

22. The method of claim 1, wherein the angiotensin (1-7) peptide is administered twice per day.

* * * * *